(12) United States Patent
    Bader

(10) Patent No.: US 10,105,252 B2
(45) Date of Patent: Oct. 23, 2018

(54) ORTHOTIC DEVICE

(71) Applicant: Wade Bader, Lutz, FL (US)

(72) Inventor: Wade Bader, Lutz, FL (US)

( * ) Notice: Subject to any disclaimer, the term of this patent is extended or adjusted under 35 U.S.C. 154(b) by 284 days.

(21) Appl. No.: 14/544,678

(22) Filed: Feb. 3, 2015

(65) Prior Publication Data
US 2016/0220406 A1    Aug. 4, 2016

(51) Int. Cl.
    *A61F 5/01*    (2006.01)
(52) U.S. Cl.
    CPC .................................. *A61F 5/0111* (2013.01)
(58) Field of Classification Search
    CPC .... A61F 5/0111; A61F 5/0127; A61F 5/0585; A61F 13/066; A61F 5/0113; A61F 5/0102; A61F 5/0116; A61F 5/05841; A61F 2007/0044; A61F 2007/0039; A43B 7/20
    See application file for complete search history.

(56) References Cited

U.S. PATENT DOCUMENTS

| | | | |
|---|---|---|---|
| 6,945,947 B2* | 9/2005 | Ingimundarson | A61F 5/0113 128/882 |
| 2007/0038169 A1* | 2/2007 | Alon | A61F 5/0111 602/27 |
| 2011/0319799 A1* | 12/2011 | Silva | A61F 5/0127 602/16 |

* cited by examiner

*Primary Examiner* — Ophelia A Hawthorne
(74) *Attorney, Agent, or Firm* — Arthur W. Fisher, III

(57) ABSTRACT

An orthotic device to align and restrict movement of the foot and ankle including an elongated lateral support member extending between an upper rigid brace member configured to engage and partially surround the upper portion of the lower leg and a lower foot support configured to engage and support the foot and a flexible leg engagement member movable between a first position and a second position extending downwardly from the upper rigid brace member terminating in a leg engagement member to selectively engage the calf portion of the patient's leg when in the second position to align and restrict movement of the foot and ankle of the patient relative to the lower leg portion of the patient.

19 Claims, 24 Drawing Sheets

ORTHOTIC DEVICE

CROSS REFERENCE

This application is a continuation-in-part of pending utility application Ser. No. 13/200,220 filed Sep. 21, 2011.

BACKGROUND OF THE INVENTION

Field of the Invention

An orthotic device to align and limit movement of the foot and ankle of a patient relative to the lower leg portion of the patient.

Description of the Prior Art

Numerous orthotic braces and devices have been designed and developed to restrict or limit movement between the lower leg and foot. Examples of such prior art are described below.

U.S. Pat. No. 7,077,818 relates to an ankle-foot orthosis comprising at least one anterior support member that extends downwardly from an upper leg engaging portion to define an anterior ankle portion which extends to a medial portion connected to a foot plate.

US 2011/0319799 discloses an ankle foot orthosis to be worn inside a common shoe that corrects ankle pronation by gently axially rotating and rolling the foot in the corrective direction by pulling from the shin assembly while further enhancing the corrective rolling with strategically placed posts on the medial edge of the sole. Rigidity of the foot assembly is paired with the flexibility of the shin assembly for donning a foot into the device when combined with a wide variety of common shoes.

US 2013/0211300 shows a hinged ankle brace having a semi-rigid ankle cuff and a semi-rigid foot bed rotatably connected by a medial hinge and a lateral hinge provides enhanced stability and support to a wearer's ankle. The medial hinge of the ankle brace may be higher than the lateral hinge to accurately replicate the bending motion of an ankle. The ankle brace also includes ratchetably interconnected semi-rigid straps. These semi-rigid straps provide a semi-rigid structure encircling the ankle of a wearer for enhanced support.

U.S. Pat. No. 3,916,886 shows a foot brace that is self-conforming and removably positionable adjacent to the posterior calf portion, the heel and instep of a leg of a user who has suffered a stroke or other disability. The brace maintains the foot of a user in a normal walking position relative to the leg. The brace is of such structure that both the foot of the user and lower portion of the brace may be disposed in a shoe without alteration or modification of the latter.

U.S. Pat. No. 5,817,041 describes a lower limb orthotic comprising a foot orthotic, a pair of lateral supporting members, a detached or removable anterior support member, a posterior support member, and strips to resist plantar flexion, dorsiflexion and various of movements of the foot and ankle.

U.S. Pat. No. 4,641,639 shows an ambulatory brace configured to fit in at least partially enclosing relation about the lower leg and foot of a patient so as to maintain this area substantially immobilized.

U.S. Pat. No. 4,834,078 relates to an orthopedic prosthesis to stabilize the tarsal joint in the case of ligament instability and to provide guidance after injuries to the ligaments comprising a foot receptacle and a leg receptacle. The foot receptacle has an opening at the point corresponding to the heel walking surface. The leg receptacle has, in the triceps plantaris muscular region, a rear opening which leaves free room for the latter.

U.S. Pat. No. 5,226,875 discloses a pair of resilient ankle braces supported to the sole, inner lining and a separately bound calf support collar of an athletic shoe. The braces include apertures shaped to accommodate protruding ankle bones. Curved lower ends of each brace mount to the heel region of the sole. Formed pockets or restraint means support the braces to the shoe liner. A separately mounted, cushioned collar restrains the upper brace end to the calf. In other constructions, one or more cushioned brace portions may be supported between the shoe and foot. In still another construction, a two-piece, hinged polymer brace is considered.

U.S. Pat. No. 5,605,535 shows an ankle positioning splint comprising a load-bearing foot brace having a bottom plate for supporting a foot in a supported position against the plate. A pair of splint arms extend upwardly from the plate and on opposite sides of the lower leg. A heel strap and an anterior ankle strap are secured to the foot brace means at opposing positions. The anterior ankle strap presses against the anterior ankle, and the heel strap presses against a specific rear portion of the heel posterior to the ankle and adjacent the calcaneus. The heel strap conforms to the natural curvature of the angled rear portion of the heel so as to apply a specific downward force into the calcaneus. A calf strap is secured to the splint arms for pressing against the angled upper section of the calf muscle. The calf strap preferably does not circumscribe the leg, and is counteracted by a front strap which presses against the front of the lower leg just below the knee. The straps and all surfaces of the brace that contact the foot and leg are heavily padded, and an optional middle strap can be disposed on the splint arms to circumscribe the leg at a location between the calf strap and the heel strap for additional support.

U.S. Pat. No. 5,176,623 describes an orthopedic brace for articulated joints of the human body comprising support members on opposite sides of the joint and a hinge assembly connected to the support members providing an axis of oscillation aligned with the axis of articulation of the joint. The hinge assembly includes retention surfaces on one hinge member and a locking device on another hinge member cooperative with the retention surfaces for supporting the joint and the associated body members in any one of plurality of fixed angle positions during normal activity for quick release from the fixed position to a free-floating condition to enable the wearer to periodically engage the therapeutic and/or rehabilitative exercise of the joint without having to remove the brace.

U.S. Pat. No. 5,269,748 teaches a therapeutic leg and foot device comprising an L-shaped member having an elongated channel-like portion configured to fit the posterior region of the lower leg and a foot portion extending integrally at right angles therefrom. When used in the correction of drop foot, the foot portion is flexed away from the perpendicular to an obtuse angle with the leg portion to conform to the deformity. In this position, the device exerts a 30 to 50 lb. pressure on the foot area to bias the foot back into normal position. There is also an equal amount of pressure or counter force on the lateral arch to correct outward turning of a foot usually associated with a foot drop deformity. This rigid flexibility also permits its use as an abulation aid in gait training.

U.S. Pat. No. 5,372,576 relates to a therapeutic device to alleviate and correct foot deformities and to maintain the foot in a fixed, stable, yet comfortable position following surgery or other medical procedure performed on the foot. The device comprises a leg engaging portion, a foot supporting portion and a heel portion which interconnects and advantageously is integral with the leg and foot portions. The heel portion has an inner and an outer surface and a curvature such that the inner surface of the heel portion can be positioned in sufficient spaced relation to the heel of a user to prevent contact between the inner surface of the heel portion and the heel of the user thereby to eliminate any chafing, or abrasive contact, or decubitus or pain-inducing pressure between the heel of the user and the inner surface of the heel portion. The side margins of the heel portion are adapted to receive releasable fastening members for engaging the foot of a user whereby the inner surface of the heel portion will be maintained in a stable, fixed position in spaced relation to the heel of a user. A one-piece liner is secured to the inside of the device which acts to provide both optimum comfort to the user and to aid in maintaining the foot of a user in the stable, fixed position established by the releasable fastenings carried on the side margins of the heel portion.

U.S. Pat. No. 5,330,419 shows an orthopedic ankle brace having a pliant boot that surrounds the ankle joint, as well as the foot and lower leg in the region thereof. The boot incorporates straps for applying compression to the ankle joint. Attached to the boot are a pair of adjustable tension straps vertically disposed about the ankle joint for restricting the mobility thereof. Integral with the boot are a pair of stiffening members positioned about the ankle joint to cooperate with the tension straps in the performance of their mobility restricting function. One or more retention straps are provided to maintain the stability of the brace.

U.S. D503,480 discloses an ornamental design for an ankle-foot orthosis.

While some of the prior art may contain some similarities relating to the present invention, none of them teach, suggest or include all of the advantages and unique features of the lower limb orthotic as the invention disclosed hereinafter.

SUMMARY OF THE INVENTION

The present invention relates to an orthotic device to align and restrict movement of the foot and ankle of a patient relative to the lower leg portion of a patient.

The orthotic device comprises an elongated rigid lateral support member disposed adjacent the outside of the patient's lower leg extending between an upper brace member including a concave inner surface configured to engage and partially surround the upper portion of the lower leg below or beneath the knee and a lower foot support including an upper surface configured to engage and support the patient's foot thereon and an inner flexible lateral alignment member moveable between a first position and a second position disposed adjacent the inside of the patient's lower leg extending downwardly from the upper brace member to selectively engage the calf portion on the inside of the patient's leg when the inner flexible lateral alignment member is in the second position.

The orthotic device is removably secured to the lower leg of the patient by an upper attachment member and a lower adjustment member.

The upper attachment member comprises a first attachment element and a second attachment element affixed to the opposite side of the upper brace member to engage each other to secure the orthotic device to the upper portion of the lower leg of the patient.

The lower adjustment member comprises a first attachment element such affixed to the side of the upper brace member and a second attachment element affixed to the opposite side of the upper brace member to engage each other to secure the orthotic device to the upper portion of the lower leg of the patient.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

As shown in FIGS. 1 through 7, the present invention relates to an orthotic device generally indicated as 10 to align and restrict movement of the foot and ankle of a patient relative to the lower leg portion of a patient.

Figure 1:
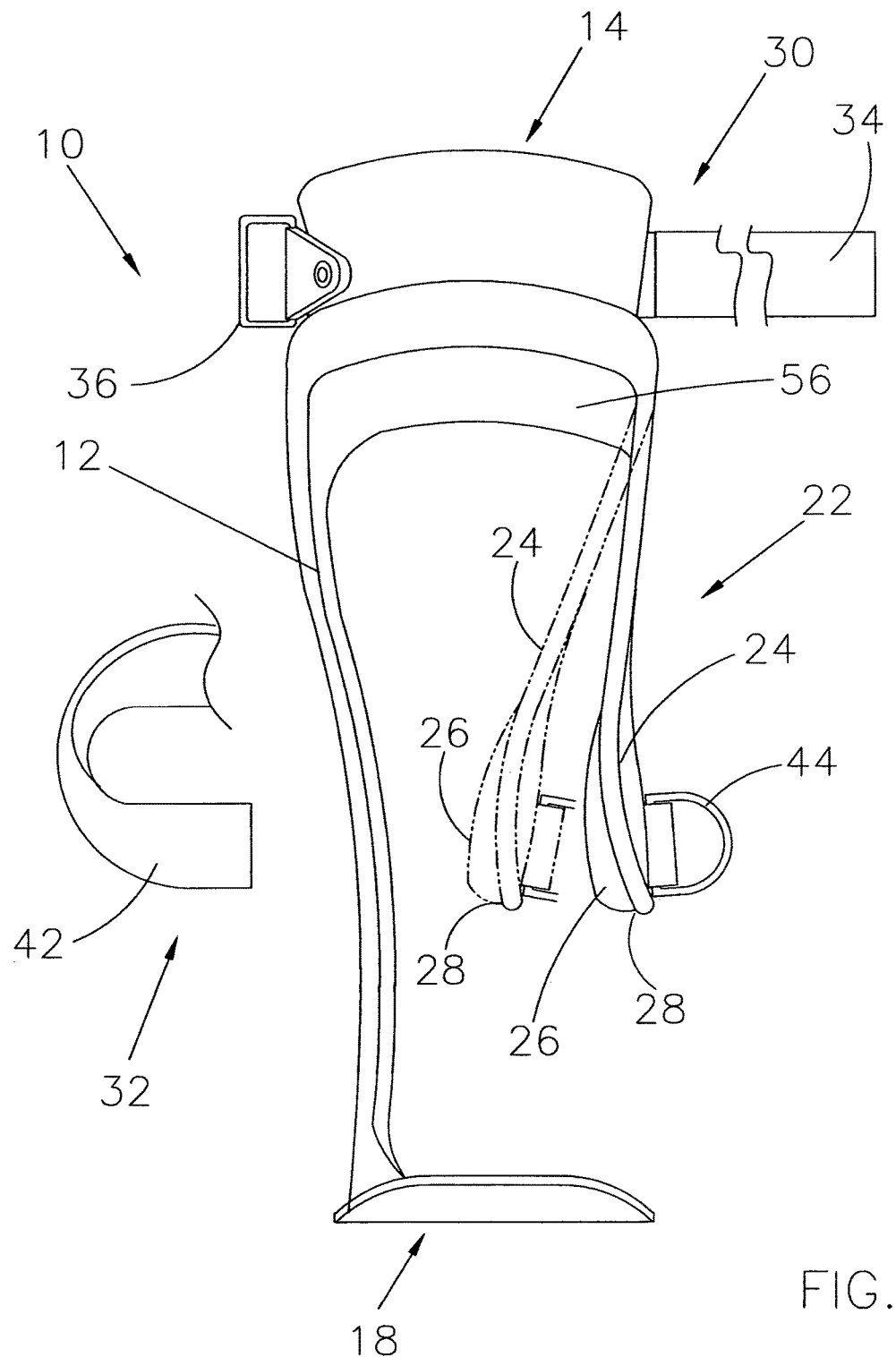
FIG. 1 is a front view of the orthotic device of the present invention.
Figure 2:
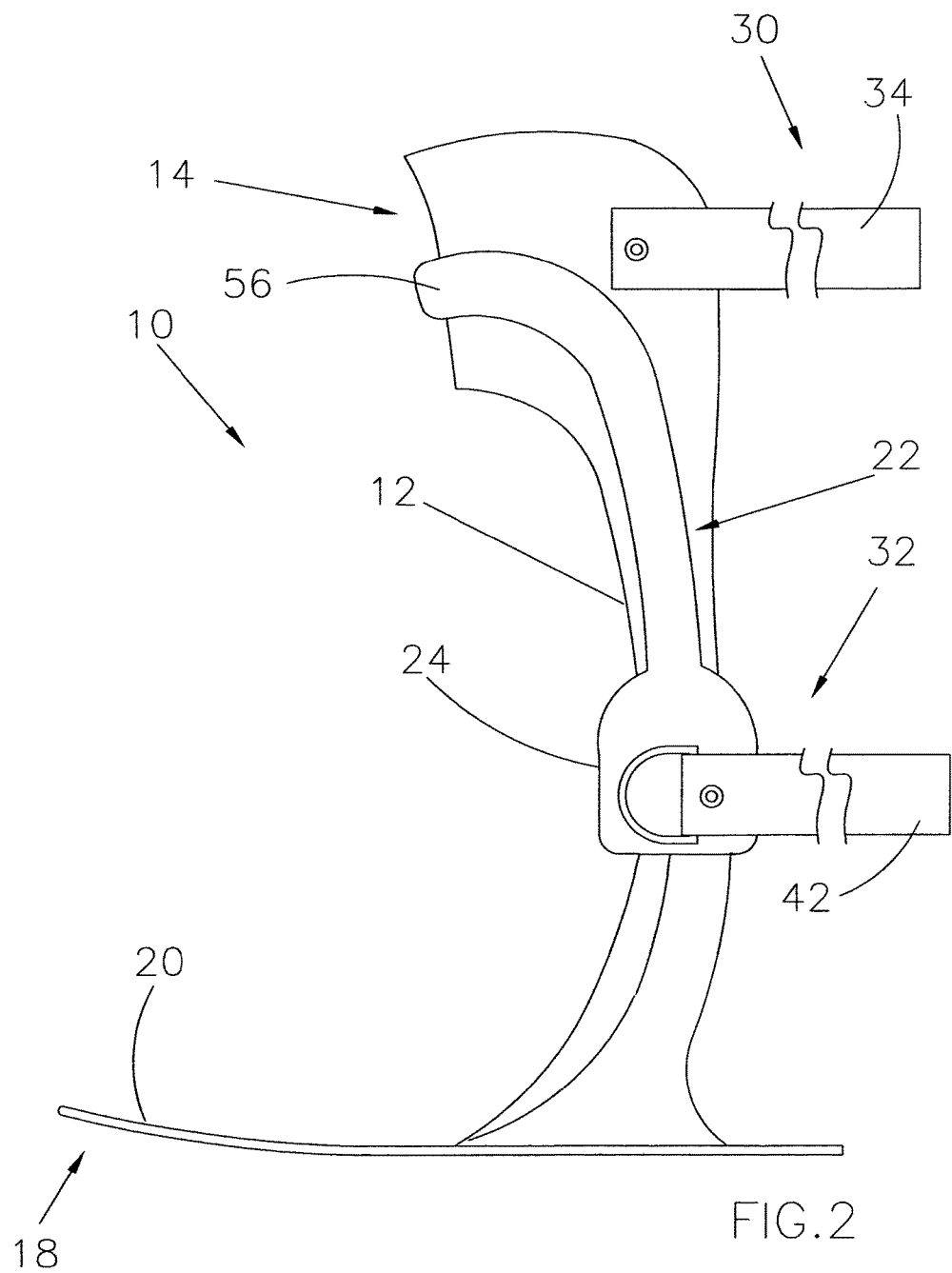
FIG. 2 is an outside side view of the orthotic device of the present invention.
Figure 3:
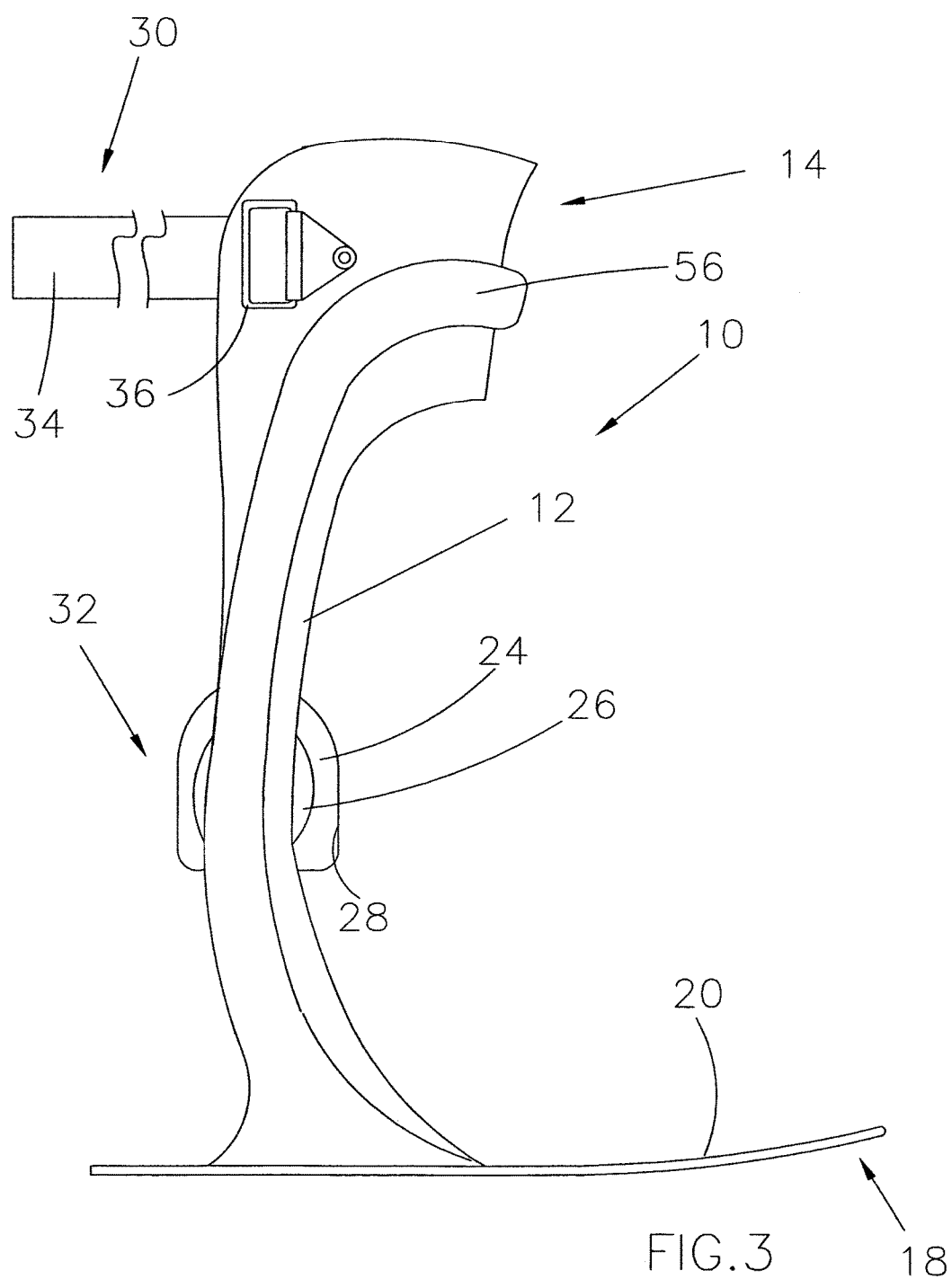
FIG. 3 is an inside side view of the orthotic device of the present invention.
Figure 4:
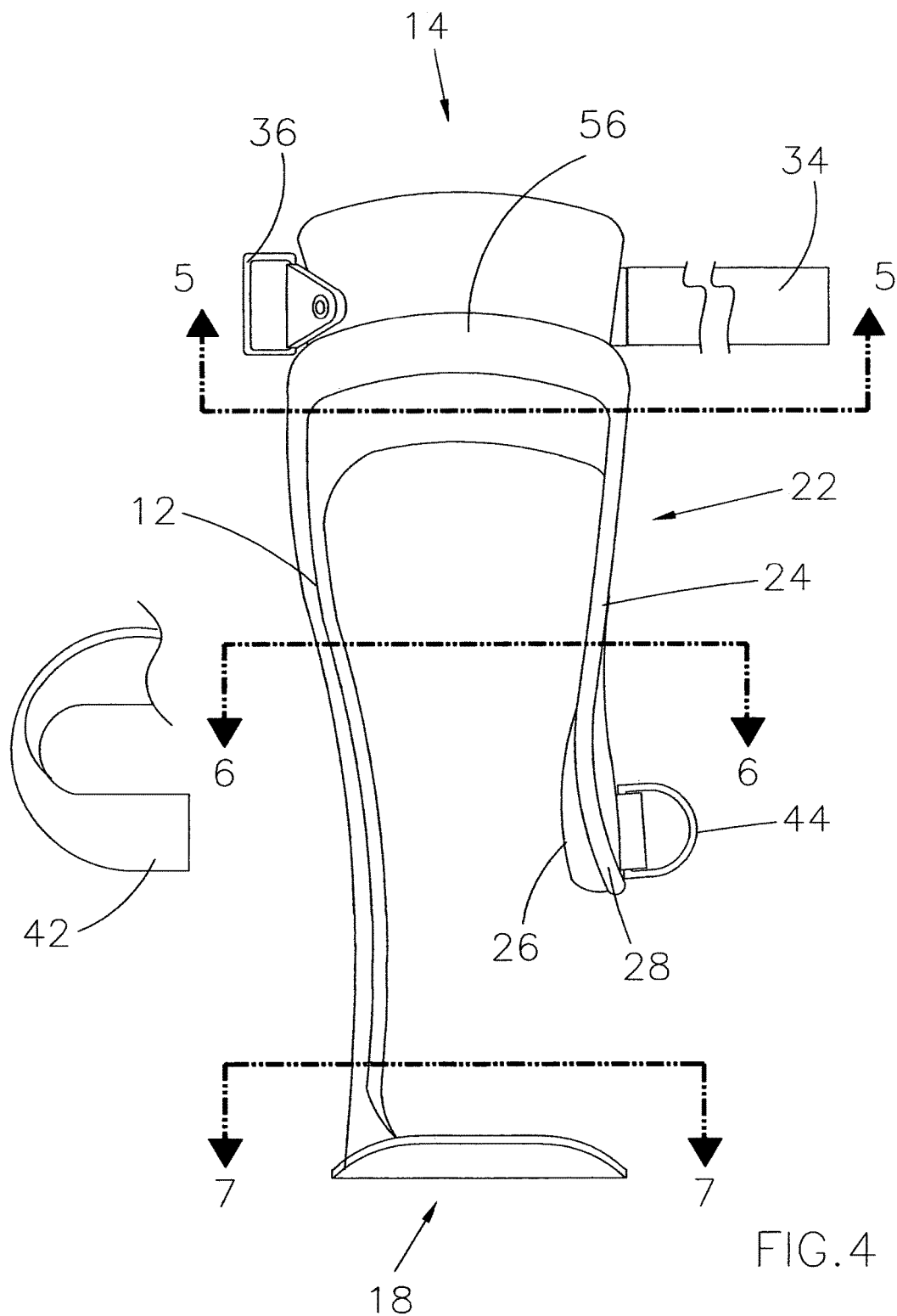
FIG. 4 is a front sectioning view of the orthotic device of the present invention.

The orthotic device 10 comprises an outer substantially vertical elongated rigid lateral support member 12 disposed adjacent the outside brace member generally indicated as 14 including a concave inner surface 16 configured to engage and partially surround the upper portion of the lower leg below or beneath the knee and a lower foot support generally indicated as 18 including an upper surface 20 configured to engage and support the patient's foot thereon and an inner substantially vertical flexible lateral alignment member generally indicated as 22 moveable between a first position and a second position disposed adjacent the inside of the patient's lower leg extending downwardly from the upper rigid brace member 14 terminating in an enlarged leg engaging member 24 having a pad or cushion 26 attached to the inner surface 28 thereof to selectively engage the calf portion on the inside of the patient's leg when the inner substantially vertical flexible lateral alignment member 22 is in the second position as shown in phantom in FIG. 1.

Figure 7:
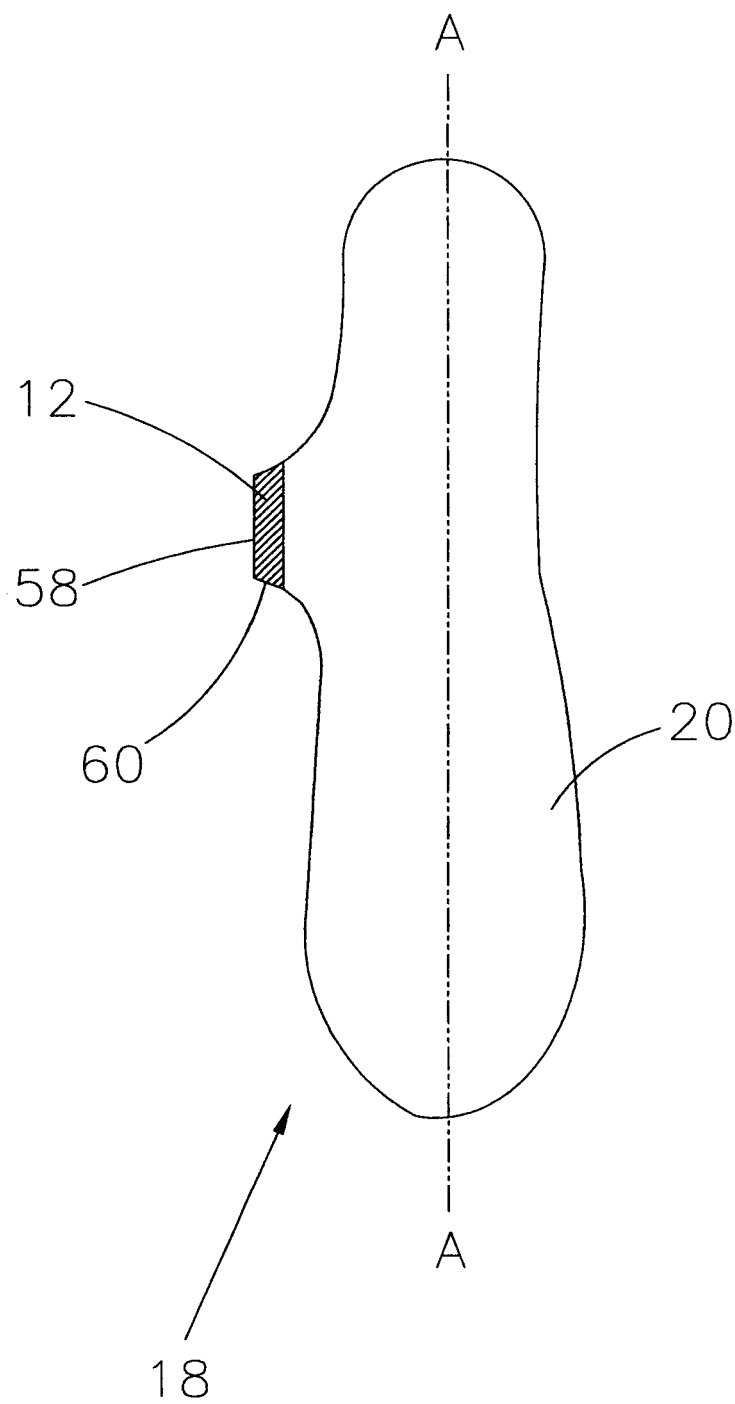
FIG. 7 is a top view of the lower foot support of the orthotic device of the present invention taken along line 7-7 of FIG. 4.

As best shown in FIG. 7, the longitudinal linear dimension 58 of the substantially vertical elongated rigid lateral support member 12 is at least twice the lateral linear dimension 60 of the substantially vertical elongated lateral support member 12 measured in the horizontal plane causing the substantially vertically elongated lateral support member 12 to be substantially rigid along the longitudinal axis AA of the lower foot support 18.

The upper substantially rigid brace member 14 may be configured to engage the front portion (anterior) of the lower leg as shown or the rear portion (posterior) of the lower leg with the upper attachment described hereinafter reversed.

The orthotic device 10 is removably secured to the lower leg of the patient by an upper attachment member generally indicated as 30 and a lower adjustment member generally indicated as 32.

Figure 5:
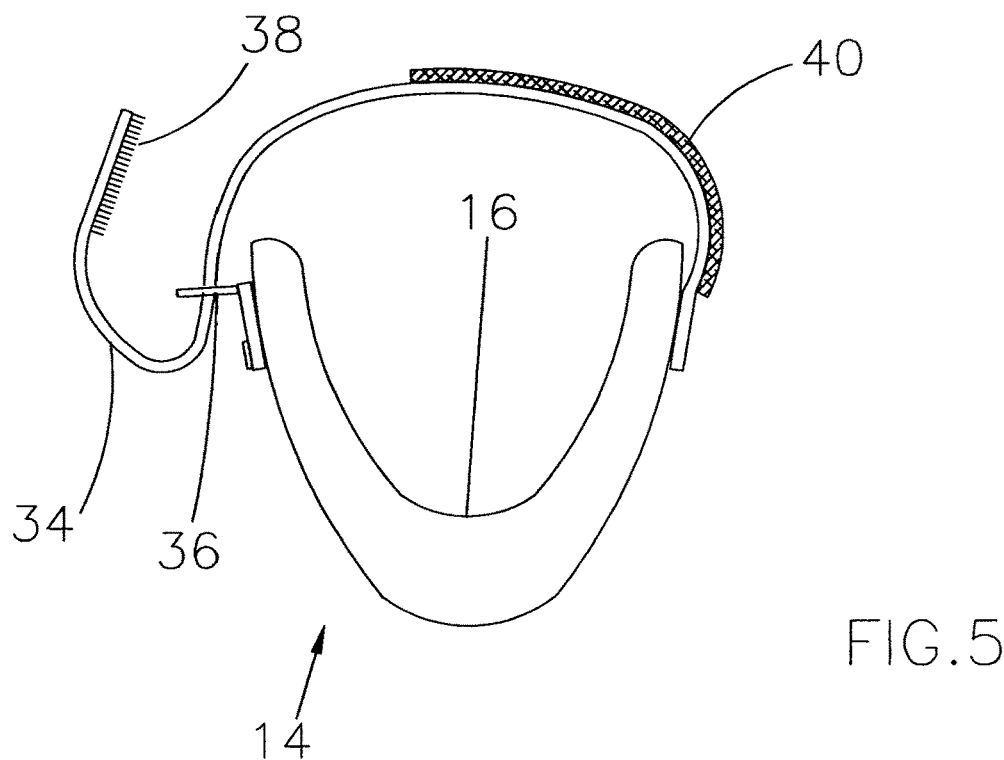
FIG. 5 is a bottom view of the upper rigid brace member and upper attachment member of the orthotic device of the present invention taken along line 5-5 of FIG. 4.

The upper attachment member 30 comprises a first attachment element 34 such as a strap affixed to the side of the upper substantially rigid brace member 14 and a second attachment element 36 such as a buckle or loop affixed to the opposite side of the upper substantially rigid brace member 14 to engage each other to strap the orthotic device 10 to the upper portion of the lower leg of the patient. As best shown in FIG. 5, the strap 34 is fed through the buckle or loop 36 and laid back on itself such that a first fastener such as a plurality of hooks 38 and a second fastener such as a plurality of loops 40 are engaged to each other to secure the upper substantially rigid brace member 14 in place.

Figure 6:
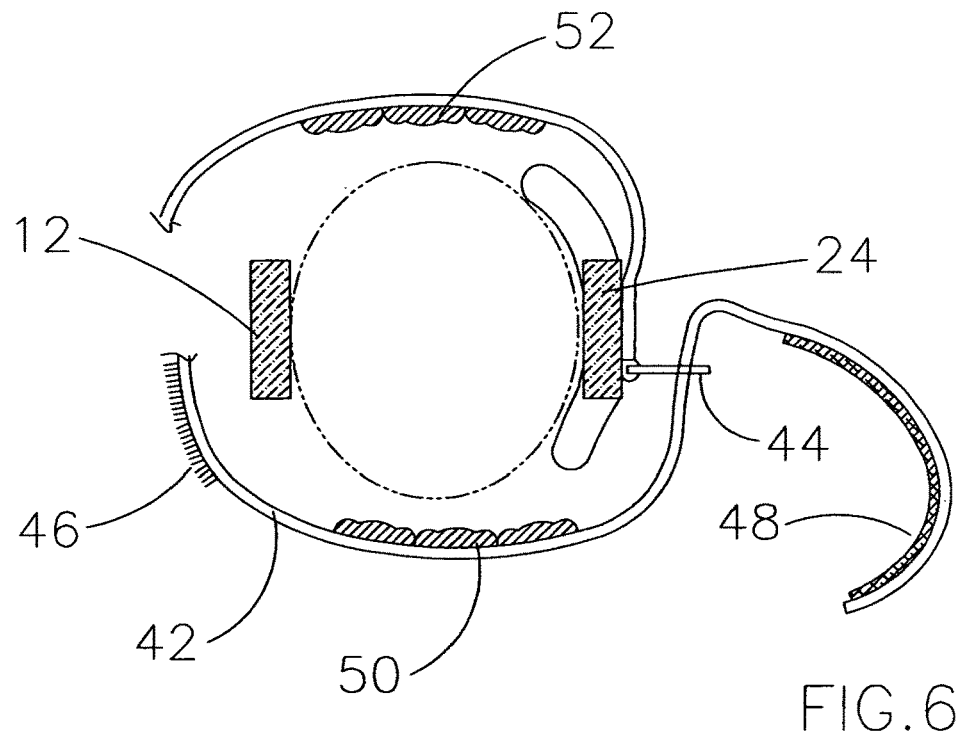
FIG. 6 is a top view of the lower adjustment member of the orthotic device of the present invention taken along line 6-6 of FIG. 4.

The lower adjustment member 32 comprises a first attachment element 42 such as a strap affixed to the side of the upper substantially rigid brace member 14 and a second attachment element 44 such as a buckle or loop affixed to the opposite side of the upper substantially rigid brace member 14 engage each other to strap the orthotic device 10 to the upper portion of the lower leg of the patient. As best shown in FIG. 6, the strap 34 is fed through the buckle or loop 36 and laid back on itself such that a first fastener such as a plurality of hooks 46 and a second fastener such as a plurality of loops 48 are engaged to each other to secure the lower adjustable member 32 in place.

In addition, an anterior cushioned restraint 50 and posterior cushioned restraint 52 are affixed to the strap 42 to secure the lower adjustment member 32 to engage the lower portion of the patient's lower leg 54.

As best shown in FIGS. 1 through 4, the outer substantially vertical elongated rigid lateral support member may include a reinforcing rib 56.

FIGS. 8 through 14 show an alternate embodiment of the present invention relating to an orthotic device generally indicated as 110 to align and restrict movement of the foot and ankle of a patient relative to the lower leg portion of a patient.

The orthotic device 110 comprises an outer substantially vertical elongated lateral support member 112 disposed adjacent the outside of the patient's lower leg extending between an upper brace member generally indicated as 114 including a concave inner surface 116 configured to engage and partially surround the upper portion of the lower leg below or beneath the knee and a lower foot support generally indicated as 118 including an upper surface 120 configured to engage and support the patient's foot thereon and an inner substantially vertical lateral alignment member generally indicated as 122 moveable between a first position and second position disposed adjacent the inside of the patient's lower leg extending downwardly from the upper brace member 114 terminating in an enlarged leg engaging member 124 having a pad or cushion 126 attached to the inner surface 128 thereof to selectively engage the calf portion on the inside of the patient's leg when the inner substantially vertical lateral alignment member 122 is in the second position as shown in phantom in FIG. 8.

Figure 11:
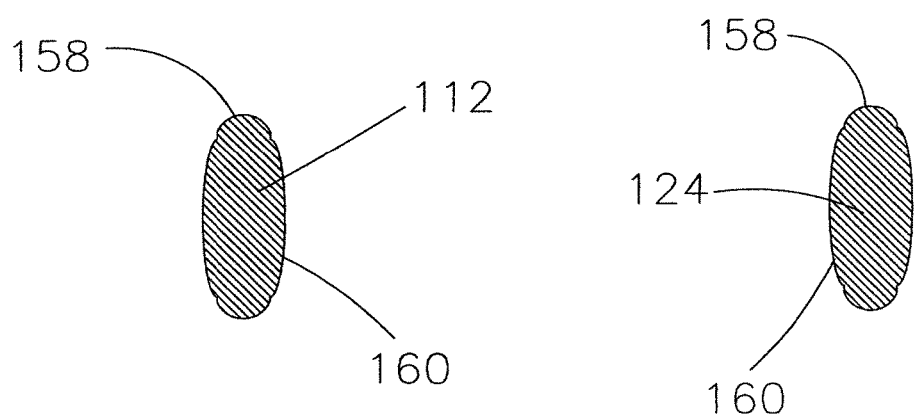
FIG. 11 is a cross-sectional view of an alternate embodiment of the orthotic device of the present invention taken along line 11-11 of FIG. 8.

As best shown in FIG. 11, the lateral linear dimension 160 of the outer substantially vertical elongated lateral support member 112 is at least about one and one-half times the longitudinal linear dimension 158 of the outer substantially vertical elongated lateral support member 112 measured in the horizontal plane allowing the outer substantially vertical elongated lateral support member 112 to flex along the longitudinal axis AA of the lower foot support 118. Preferably the lateral linear dimension 160 of the outer substantially vertical elongated lateral support member 112 is at least about ⅜ inch.

The upper brace member 114 may be configured to engage the front portion or anterior of the lower leg as shown or the rear portion or posterior of the lower leg with the upper attachment described hereinafter reversed.

The orthotic device 110 is removably secured to the lower patient by an upper attachment member generally indicated as 130 and a lower adjustment member generally indicated as 132.

Figure 12:
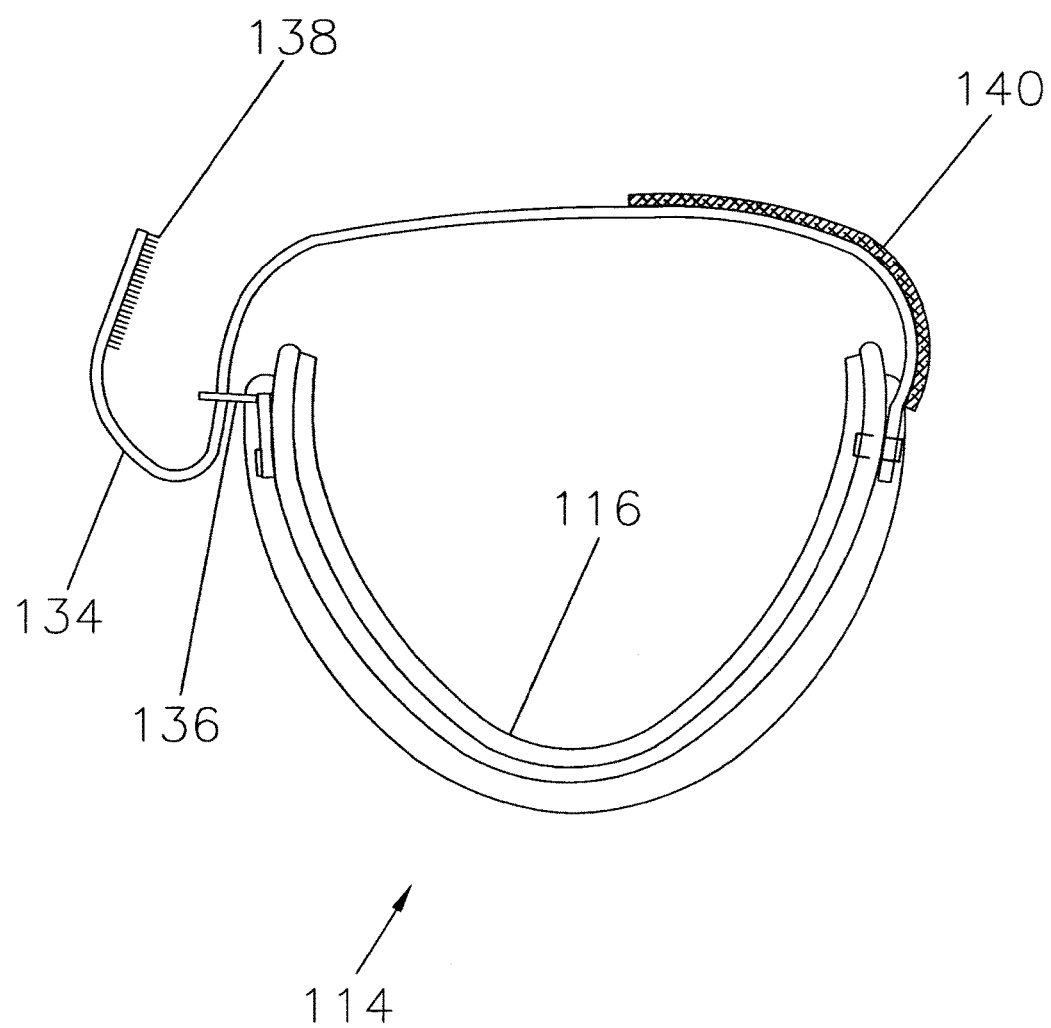
FIG. 12 is a bottom view of the upper brace member and upper attachment member of the alternate embodiment of the orthotic device of the present invention taken along line 12-12 of FIG. 8.

The upper attachment member 130 comprises a first attachment element 134 such as a strap affixed to the side of upper brace member 114 and a second attachment element 136 such as a buckle or loop affixed to the opposite side of the upper brace member 114 to engage each other to strap the orthotic device 110 to the upper portion of 20 the lower leg of the patient. As best shown in FIG. 12, the strap 134 is fed through the buckle or loop 136 and laid back on itself such that a first fastener such as a plurality of hooks 138 and a second fastener such as a plurality of loops 140 are engaged to each other to secure the upper brace member 114 in place. The upper brace member 114 may comprise a rigid material flexible enough to fit or engage the outside contour of the patient's leg held in place by the upper attachment member 130.

Figure 13:
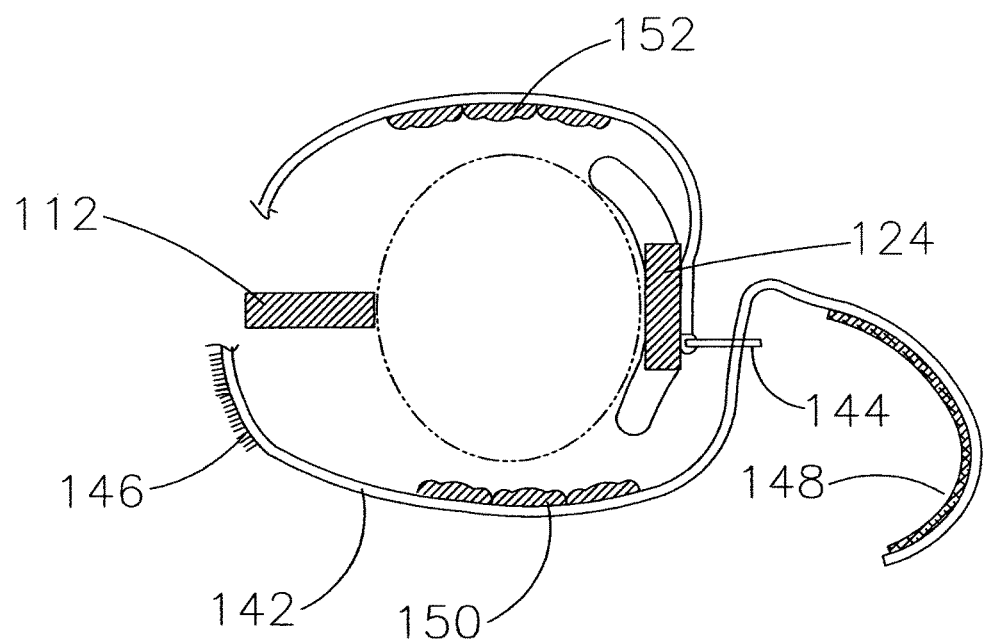
FIG. 13 is a top view of the lower adjustment member of the alternate embodiment of the orthotic device of the present invention taken along line 13-13 of FIG. 8.
Figure 14:
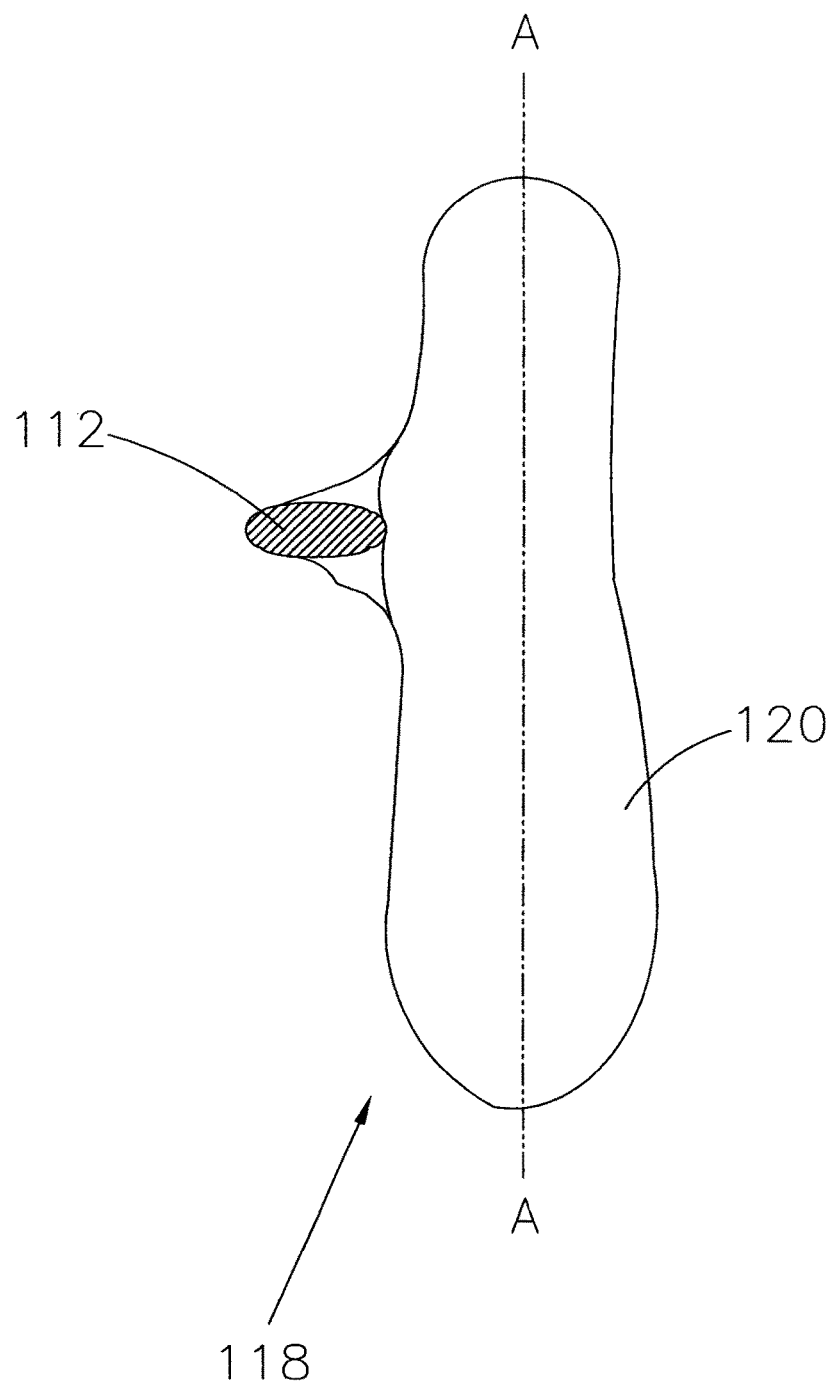
FIG. 14 is a top view of the lower foot support of the alternate embodiment of the orthotic device of the present invention taken along line 14-14 of FIG. 8.

The lower adjustment member 132 comprises a first attachment element 142 such as a strap affixed to the side of the upper brace member 114 and a second attachment element 144 such as a buckle or loop affixed to the opposite side of the upper brace member 114 to engage each other to strap the orthotic device 110 to the upper portion of the lower leg of patient. As best shown in FIG. 13, the strap 134 is fed through the buckle or loop 136 and laid back on itself such that a first fastener such as a plurality of hooks 146 and a second fastener such as a plurality of loops 148 are engaged to each other to secure the lower adjustable member 132 in place.

In addition, an anterior cushioned restraint 150 and posterior cushioned restraint 152 are affixed to the strap 142 to secure the lower adjustment member 132 to engage the lower portion of the patient's lower leg 154.

Figure 8:
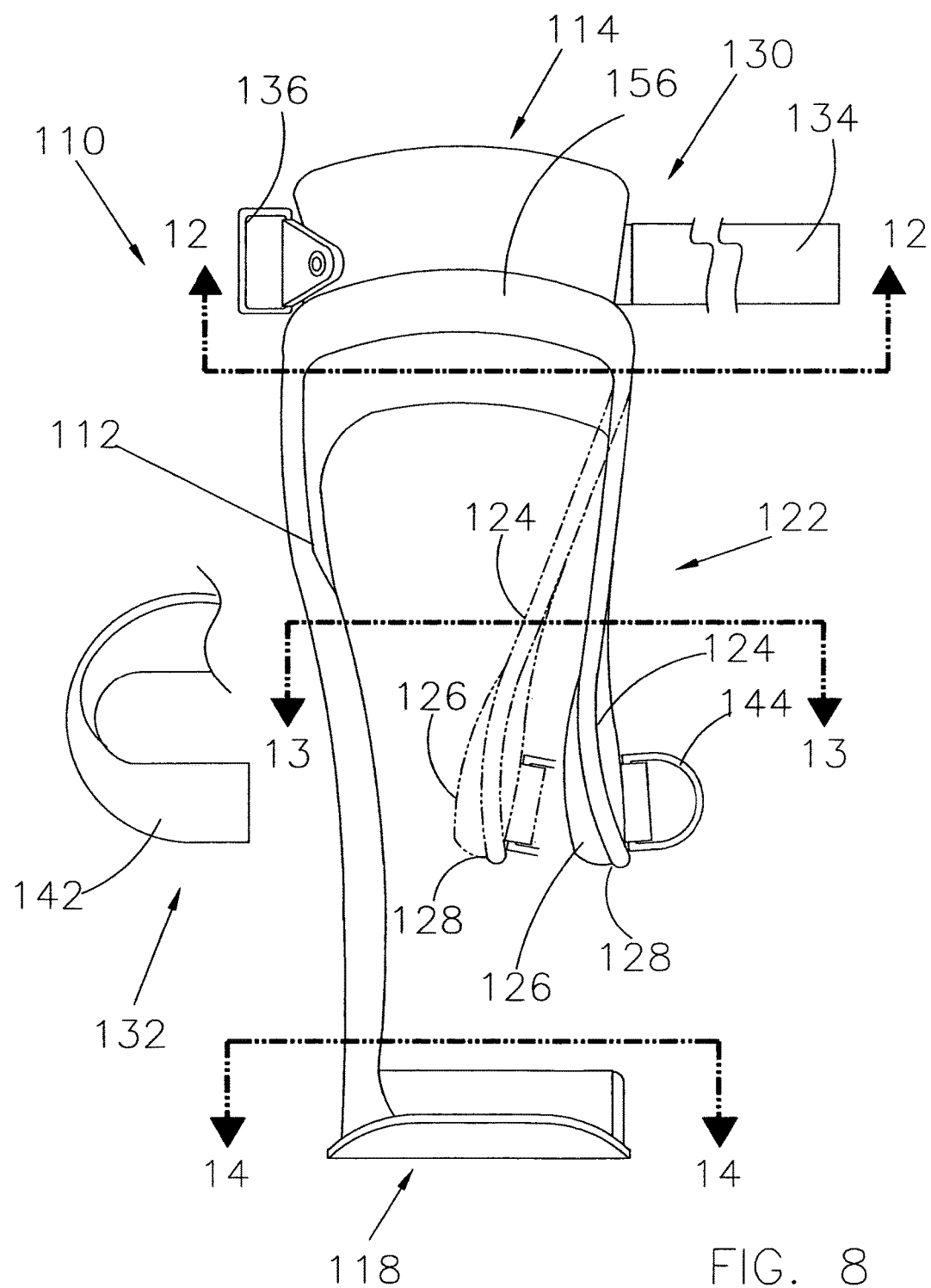
FIG. 8 is a front view of an alternate embodiment of the orthotic device of the present invention.
Figure 9:
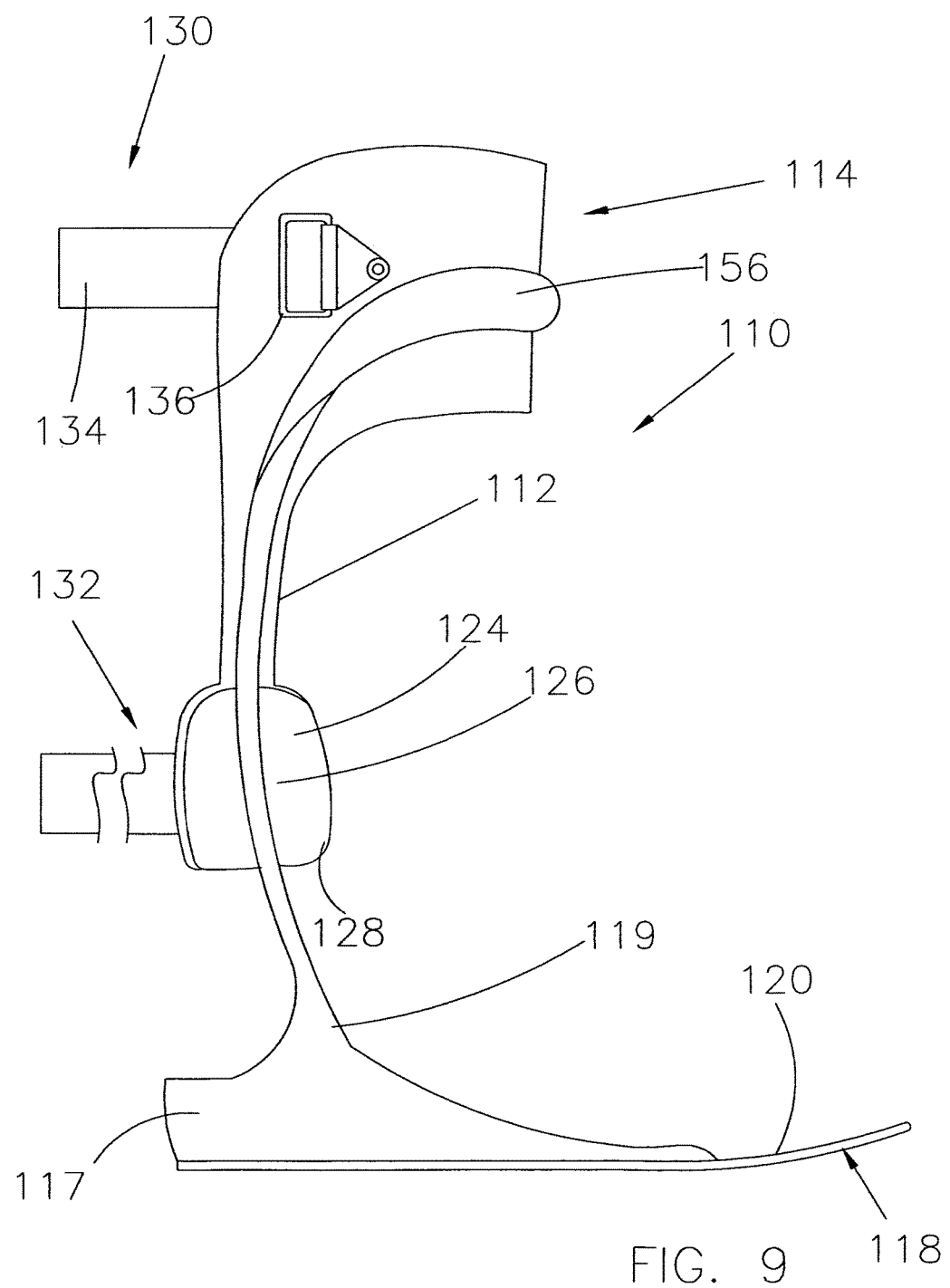
FIG. 9 is an inside side view of an alternate embodiment of the orthotic device of the present invention shown in FIG. 8.
Figure 10:
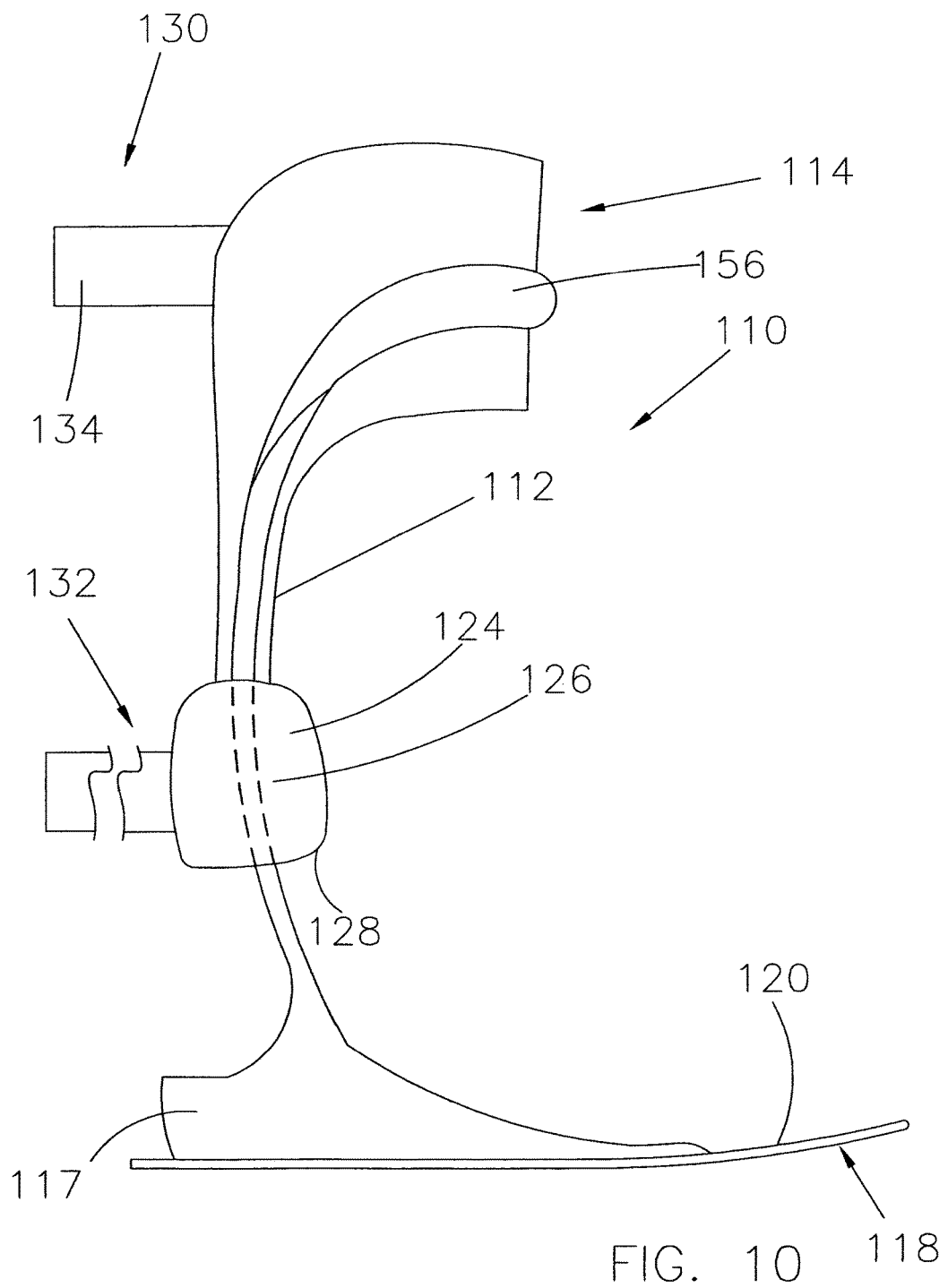
FIG. 10 is an outside side view of an alternate embodiment of the orthotic device of the present invention shown in FIG. 8.

As best shown in FIGS. 8 through 10, the outer substantially vertical elongated lateral support member 112 may include a reinforcing rib 156.

FIGS. 15 through 21 show another alternate embodiment of the present invention relating to an orthotic device generally indicated as 210 to align and restrict movement of the foot and ankle of a patient relative to the lower leg portion of a patient.

The orthotic device 210 comprises an inner substantially vertical elongated lateral support member 212 disposed adjacent the inside of the patient's lower leg extending between an upper brace member generally indicated as 214 including a concave inner surface 216 configured to engage and partially surround the upper portion of the lower leg below or beneath knee and a lower foot support generally indicated as 218 including an upper surface 220 configured to engage and support the patient's foot thereon and an outer substantially vertical lateral alignment member generally indicated as 222 movable between a first position and a second position disposed adjacent the outside of the patient's lower extending downwardly from the upper brace member 214 terminating in an enlarged leg engaging member 224 having a pad or cushion 226 attached to the inner surface 228 thereof to selectively engage the calf portion on the outside of the patient's leg when the outer substantially vertical lateral alignment member 222 is in the second position as shown in phantom in FIG. 15.

Figure 18:
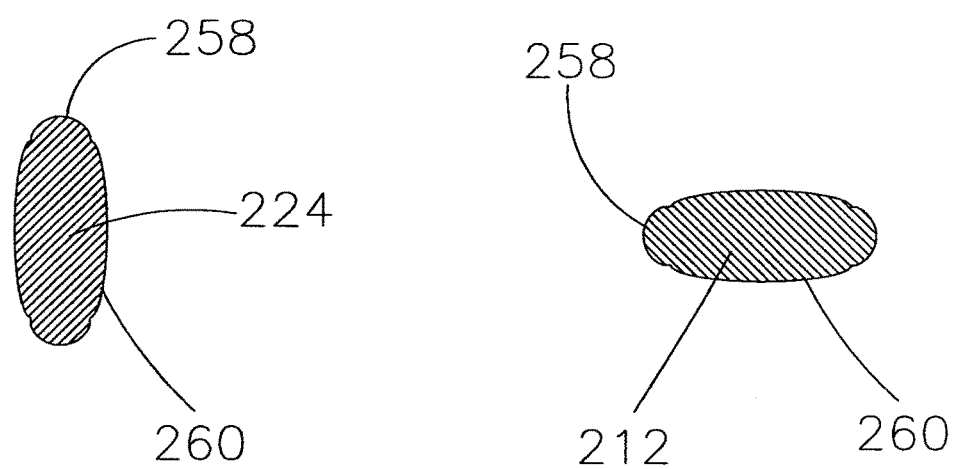
FIG. 18 is a cross-sectional top view of the alternate embodiment of the orthotic device of the present invention taken along line 18-18 of FIG. 15.

As best shown in FIG. 18, the lateral linear dimension 260 of the inner substantially vertical elongated lateral support member 212 at least about one and one-half times the longitudinal linear dimension 258 of the inner substantially vertical elongated lateral support member 212 measured in the horizontal plane allowing the inner substantially vertical elongated lateral support member 212 to flex along the longitudinal axis AA of the lower foot support 218. Preferably the lateral linear dimension 260 of the outer substantially vertical elongated lateral support member 222 is at least about ⅜ inch.

The upper brace member 214 may be configured to engage the front portion or anterior of the lower leg as shown or the rear portion or posterior of the lower leg with the upper attachment described hereinafter reversed.

The orthotic device 210 is removably secured to the lower leg of the patient by an upper attachment member generally indicated as 230 and a lower adjustment member generally indicated as 232.

Figure 19:
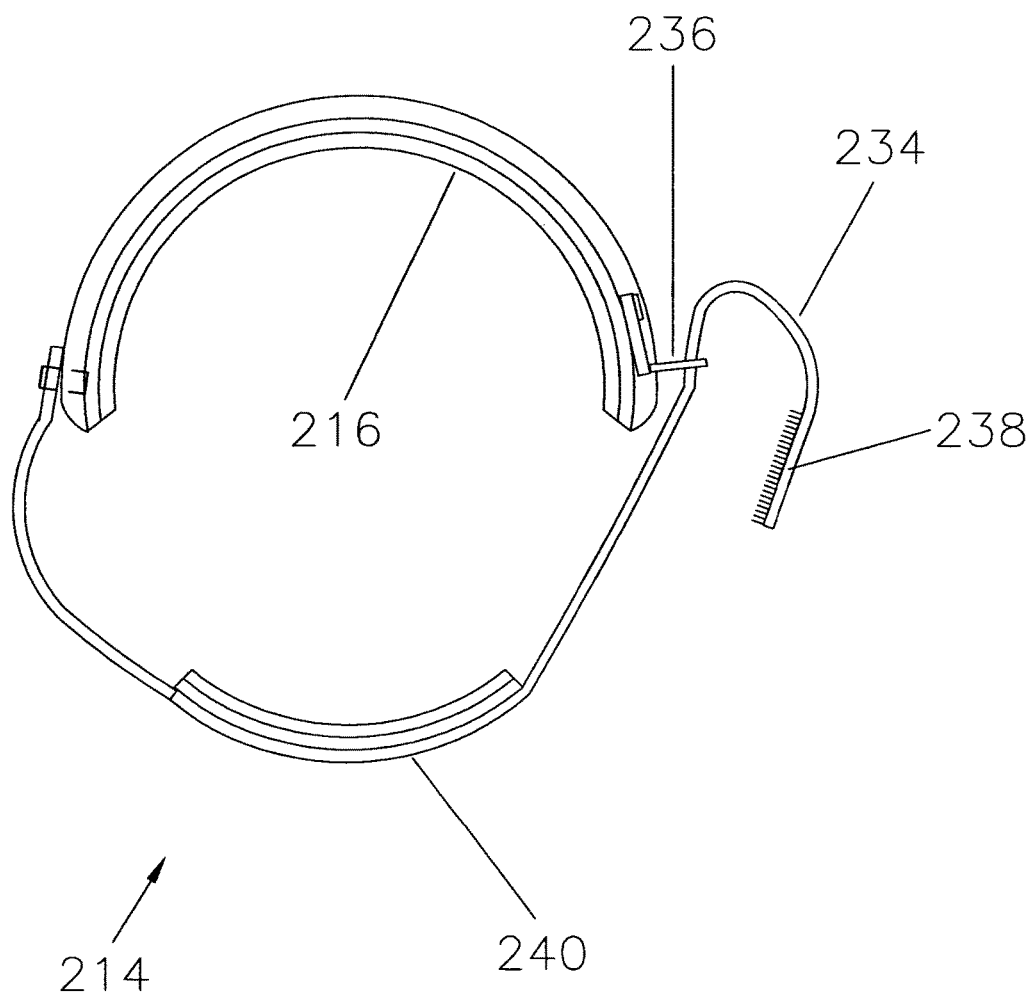
FIG. 19 is a bottom view of the upper brace member and upper attachment member of the alternate embodiment of the orthotic device of the present invention taken along line 19-19 of FIG. 15.

The upper attachment member 230 comprises a first attachment element 234 such as a strap affixed to the side of the upper brace member 224 and a second attachment element 236 such as a buckle or loop affixed to the opposite side of the upper brace member 224 to engage each other to strap the orthotic device 210 to the upper portion of the lower leg of the patient. As best shown in FIG. 19, the strap 234 is fed through the buckle or loop 236 and laid back on itself such that a first fastener such as a plurality of hooks 238 and a second fastener such as a plurality of loops 240 are engaged to each other to secure the upper brace member 224 in place. The upper brace member 224 may comprise a rigid material flexible enough to fit or engage the outside contour of the patient's leg held in place by the upper attachment member 230.

Figure 20:
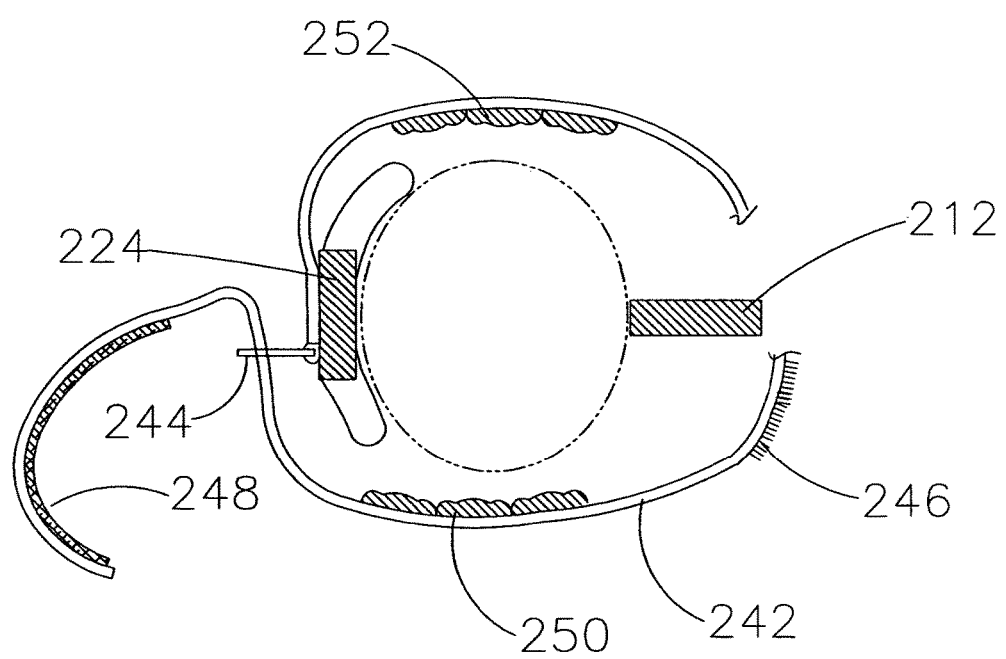
FIG. 20 is a top view of the lower adjustment member of the alternate embodiment of the orthotic device of the present invention taken along line 20-20 of FIG. 15.
Figure 21:
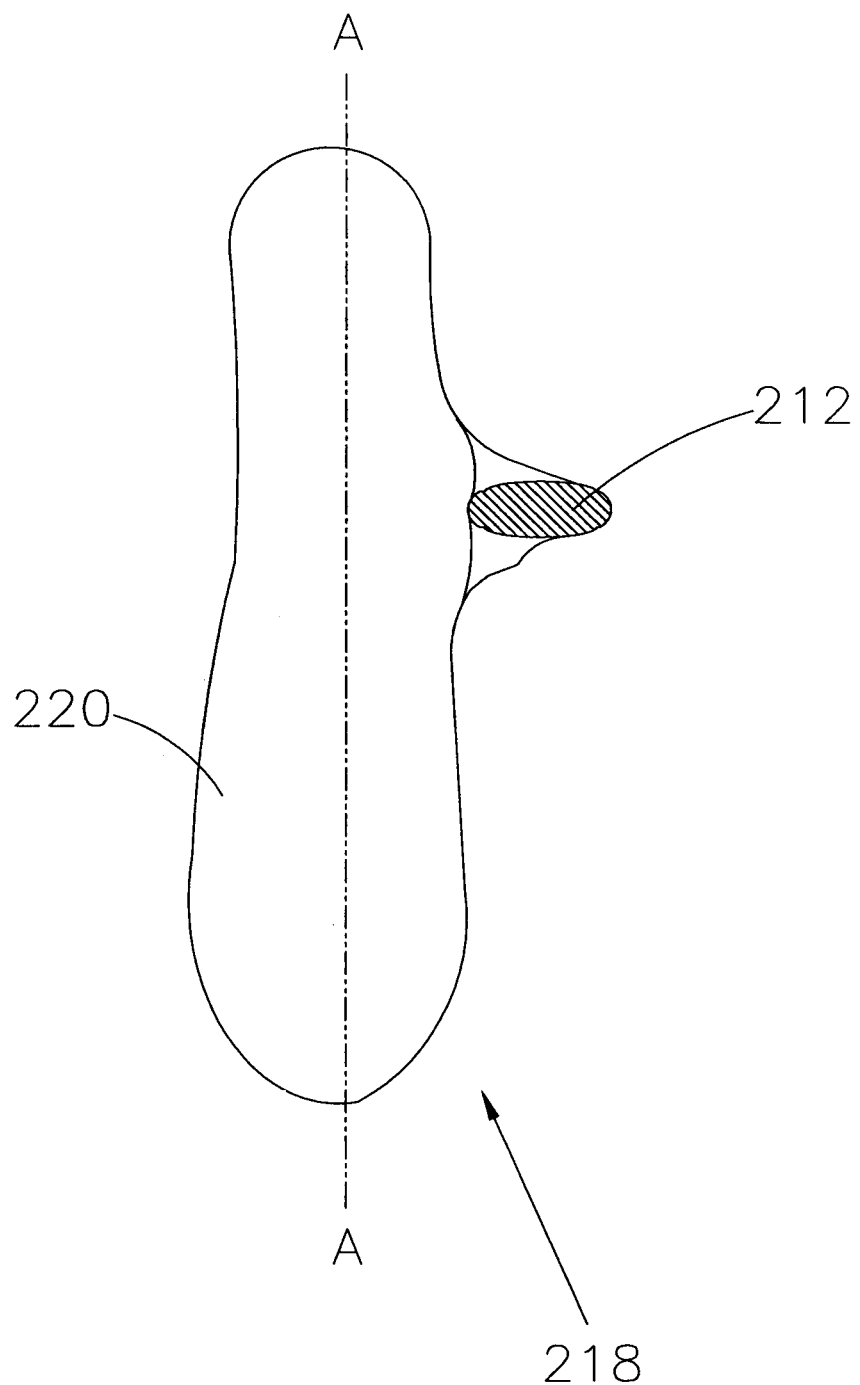
FIG. 21 is a top view of the lower foot support of the alternate embodiment of the orthotic device of the present invention taken along line 21-21 of FIG. 15.

The lower adjustment member 232 comprises a first attachment element 242 such as a strap affixed to the side of the upper brace member 224 and a second attachment element 244 such as a buckle or loop affixed to the opposite side of the upper brace member 224 to engage each other to strap the orthotic device 210 to the upper portion of the lower leg of the patient. As best shown in FIG. 20, the strap is fed through the buckle or loop 236 and laid back on itself such that a first fastener such as a plurality of hooks 246 and a second fastener such as plurality of loops 248 are engaged to each other to secure the lower adjustable member 232 in place.

In addition, an anterior cushioned restraint 250 and posterior cushioned restraint 252 are affixed to the strap 242 to secure the lower adjustment member 232 to engage the lower portion of the patient's lower leg 254.

Figure 15:
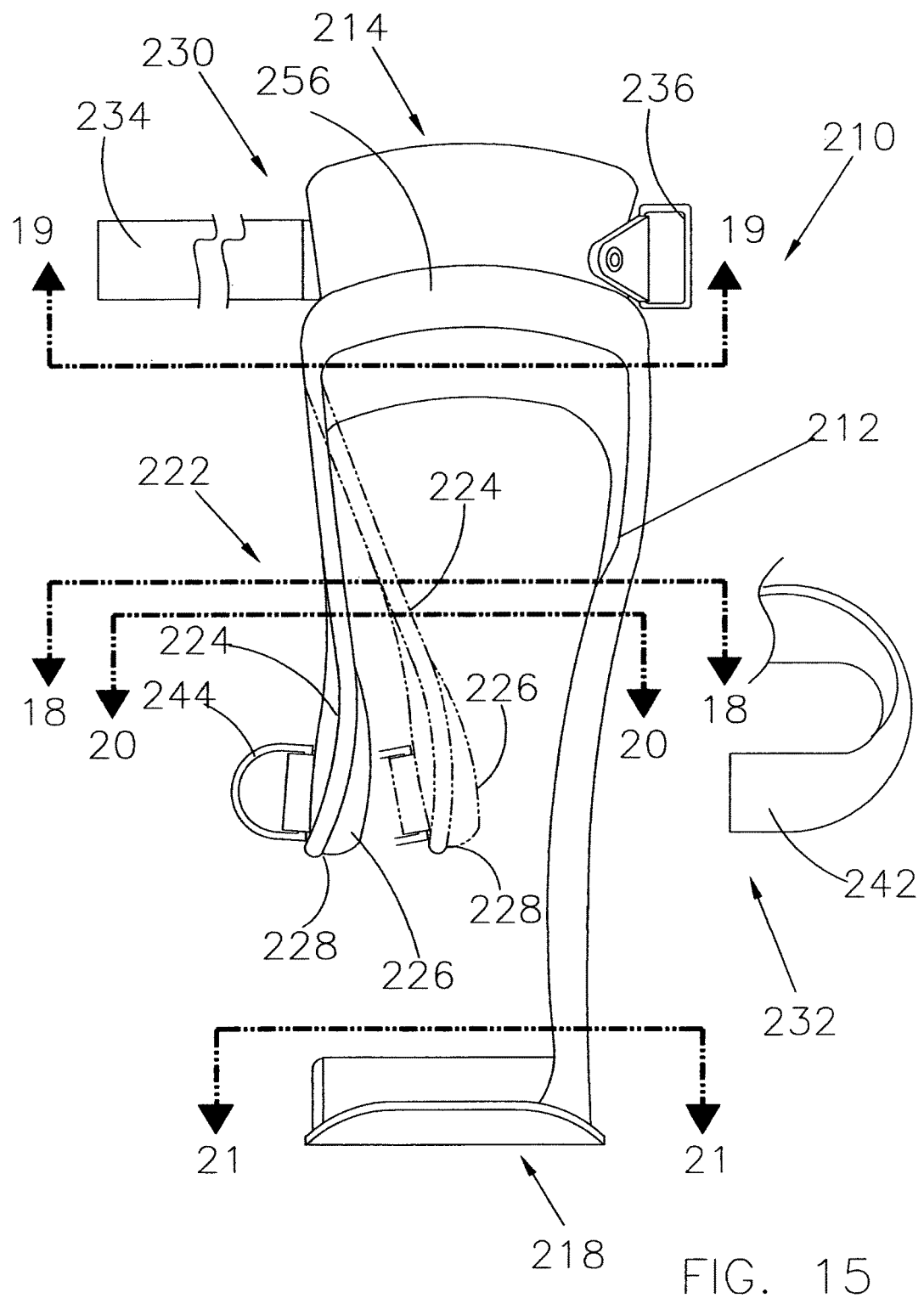
FIG. 15 is a front view of another alternate embodiment of the orthotic device of the present invention.
Figure 16:
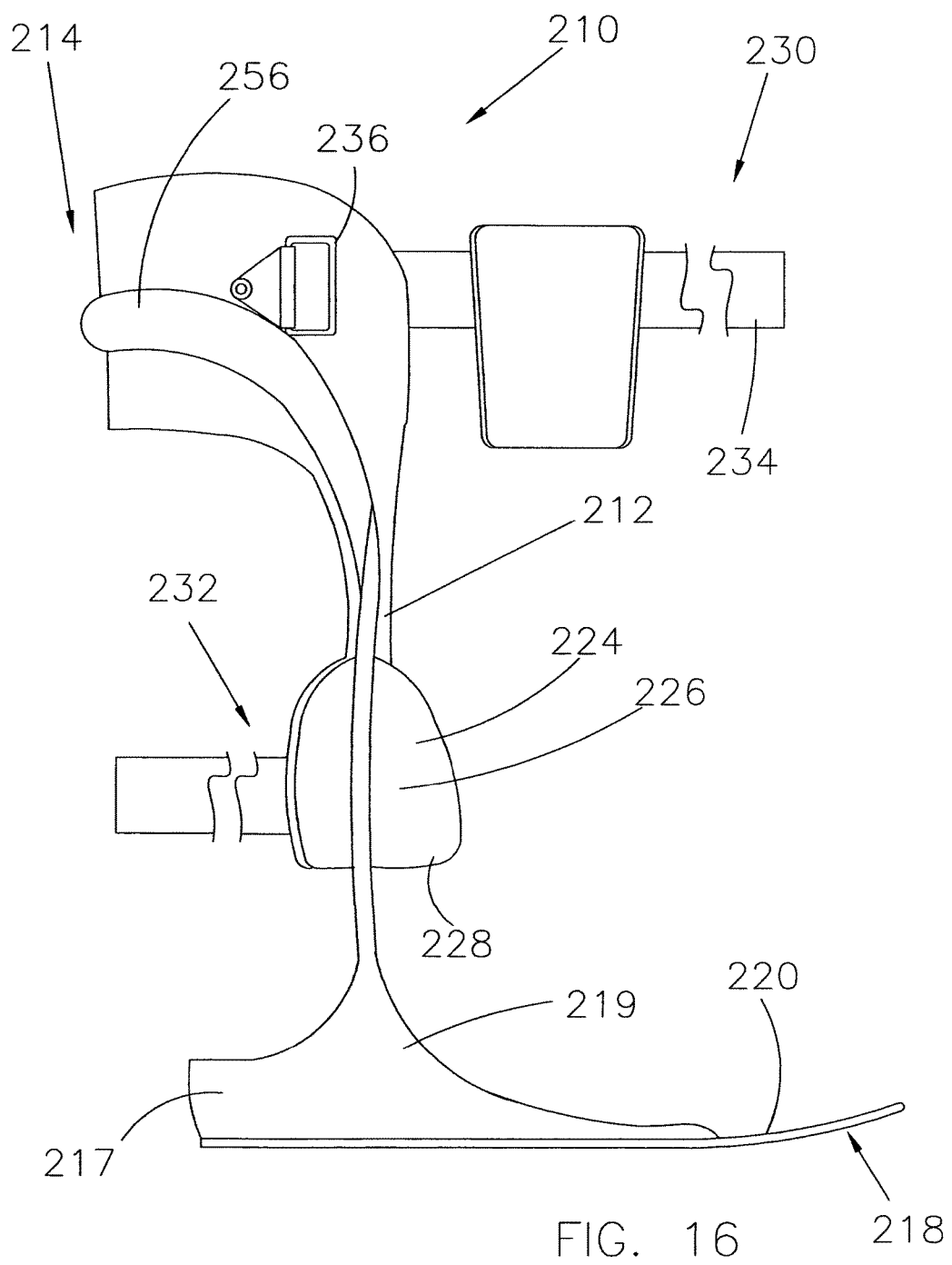
FIG. 16 is an inside side view of the orthotic device of the present invention shown in FIG. 15.
Figure 17:
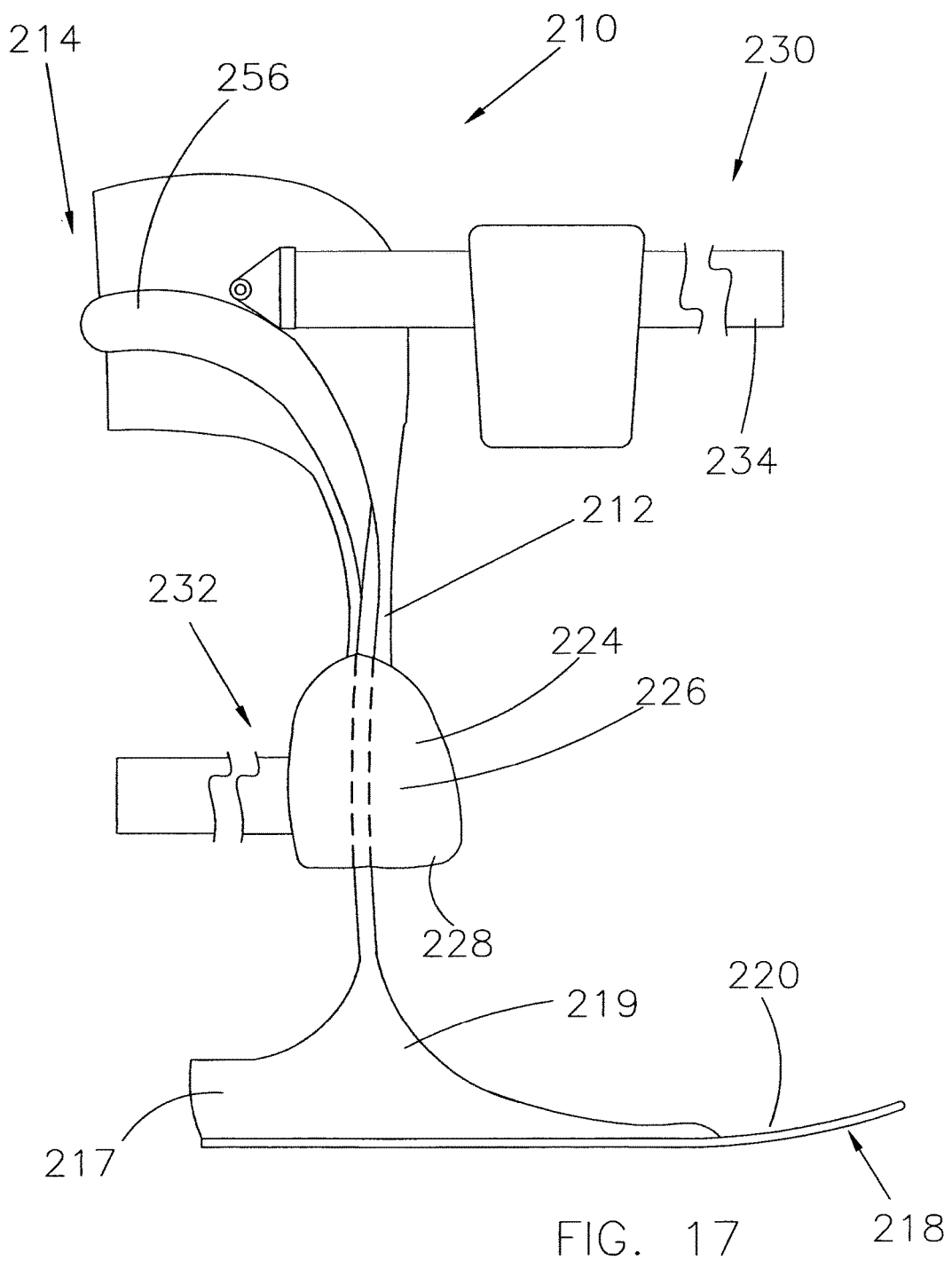
FIG. 17 is an outside side view of the orthotic device of the present invention shown in FIG. 15.

As best shown in FIGS. 15 through 17, the inner substantially vertical elongated lateral support member 212 may include a reinforcing rib 256.

The embodiments depicted in FIGS. 8 and 15 allow the substantially vertical elongated lateral support members 112 and 212 to flex along the longitudinal axis AA of the lower foot support 118 and 218.

Figure 22:
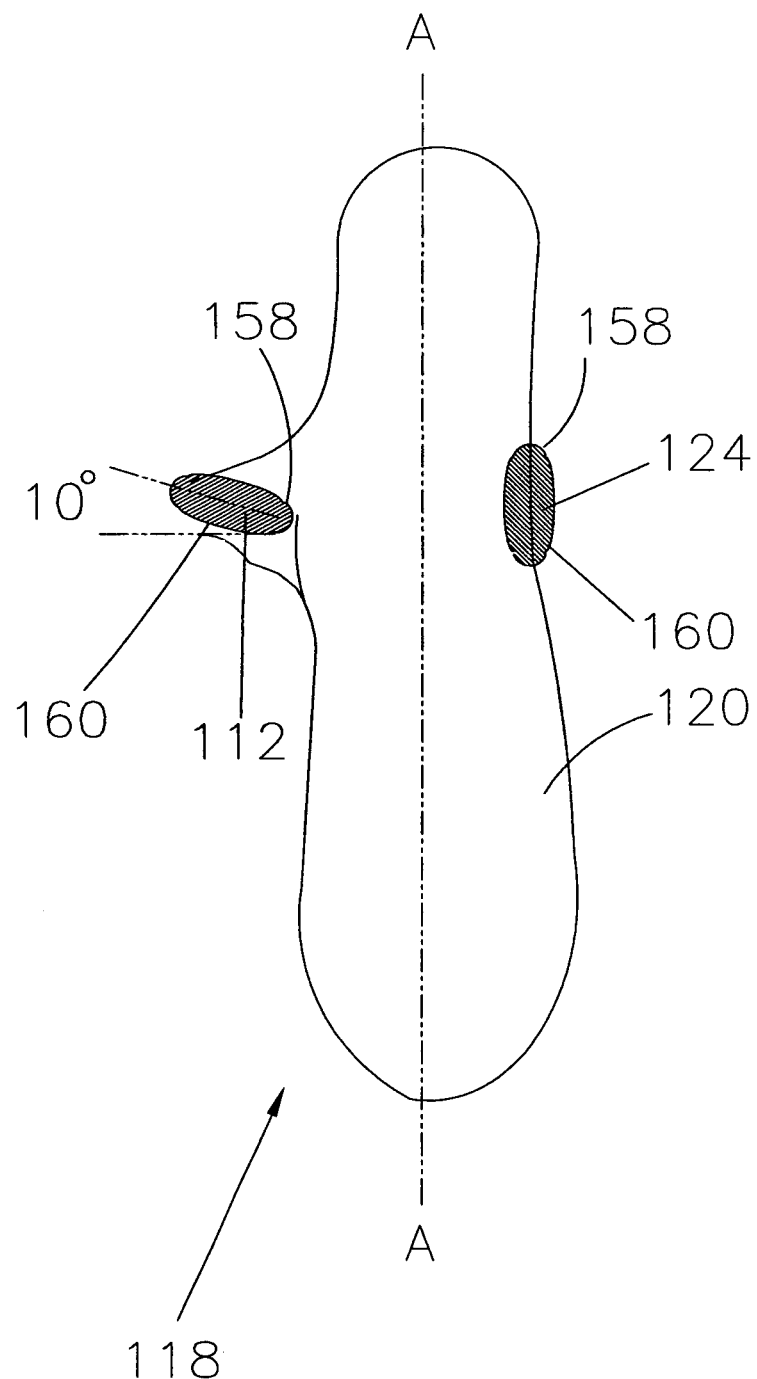
FIG. 22 is a cross-sectional top view of the substantially vertical elongated lateral support member and substantially vertical flexible lateral alignment member of the present invention with the substantially vertical elongated lateral support member inclined in a second direction or toe in relative to longitudinal axis AA of the lower foot support.

As shown in FIG. 22, the substantially vertical elongated lateral support member 112 may be inclined in a first or toe out direction relative to the longitudinal axis AA of the lower foot support 118 such that the patient's foot are rotated and held in an outwardly direction.

Figure 23:
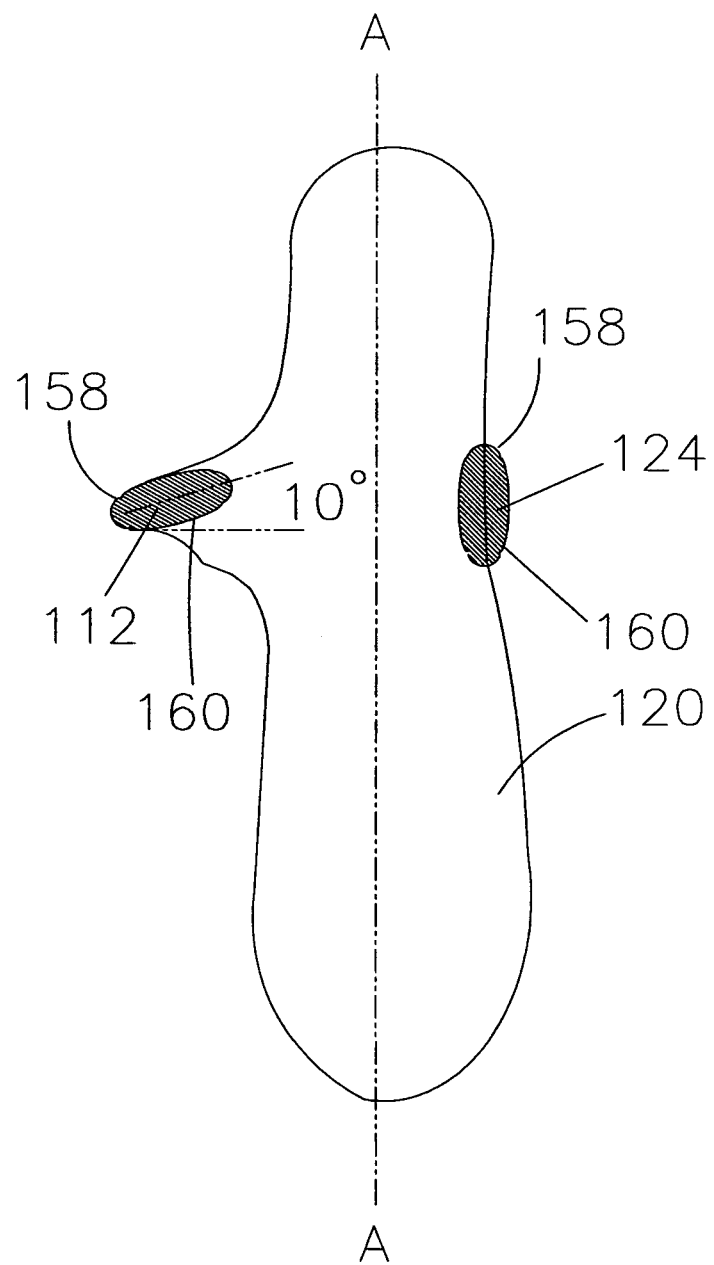
FIG. 23 is a cross-sectional top view of the substantially vertical elongated lateral support member and substantially vertical flexible lateral alignment member of the present invention with the substantially vertical elongated lateral support member inclined in a first direction or toe out relative to longitudinal axis AA of the lower foot support.

As shown in FIG. 23, the substantially vertical elongated lateral support member 112 may be inclined in a second direction or toe in relative to the longitudinal axis AA of the lower foot support 118 such that the patient's foot are held in an inwardly direction.

As shown in FIGS. 9 and 16, the lower foot supports 118 and 218 may comprise a heel cup 117 and 217 respectively extending upwardly from the rear portion of the top surface 120 and 220 respectively. In addition, a lateral support member mounts 119 and 219 respectively extend upwardly from the heel cups 117 and 217 respectively to couple the substantially vertical elongated lateral support members 112 and 212 respectively to the lower foot supports 118 and 218 respectively such that the lower portion of the substantially vertical elongated lateral support members 112 and 212 respectively are substantially aligned with the patient's ankle at the point of flexure of the substantially vertical elongated lateral support members 112 and 212 respectively.

The various embodiments restrict the lateral movement of the foot and lower leg portion having a substantially vertical lateral support member and plate to be disposed adjacent one side of a patient's lower leg and a substantially vertical laterally flexible engagement member to engage the opposite side of the patient's lower leg.

Figure 24:
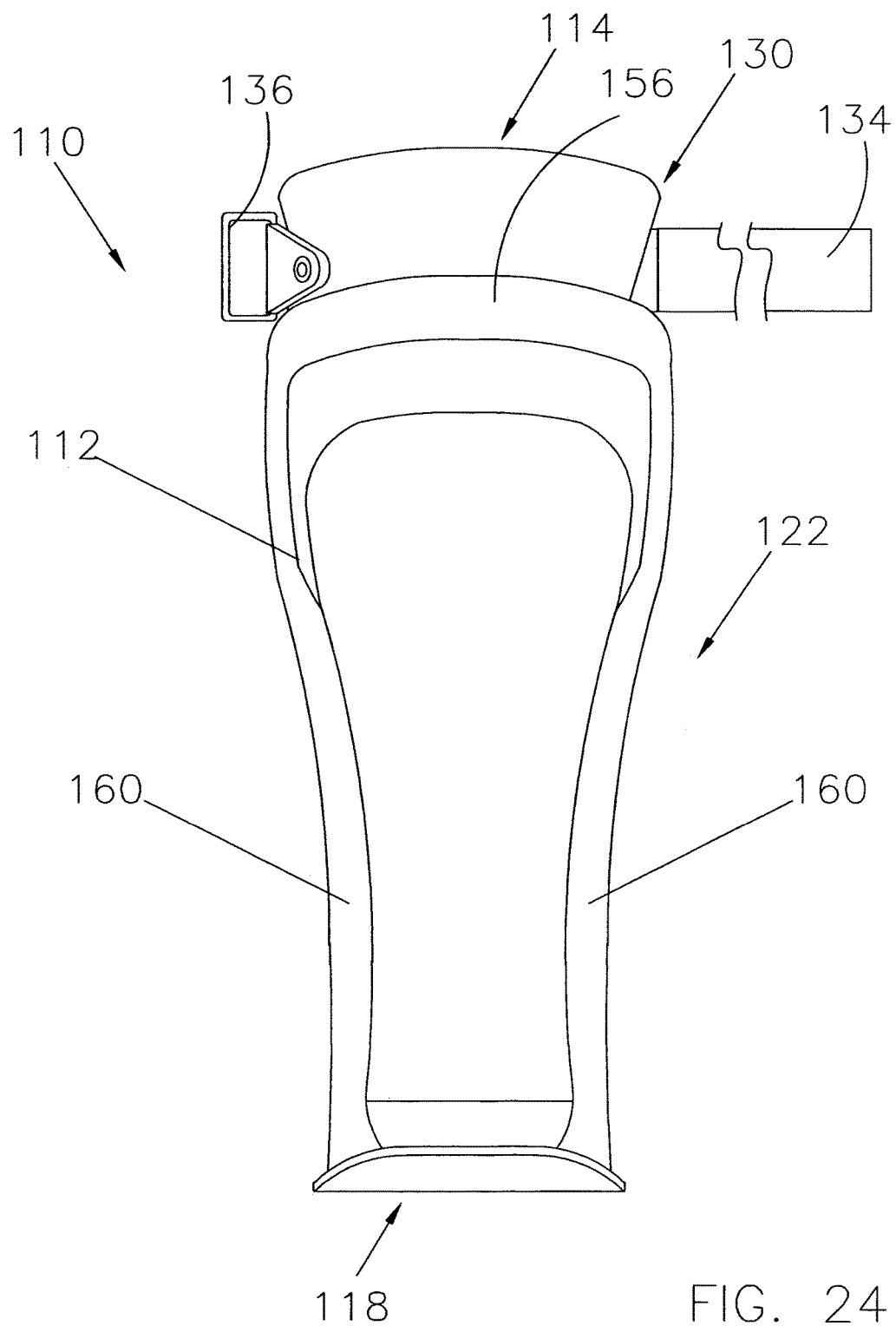
FIG. 24 is a front view of still another alternate embodiment of the orthotic device of the present invention.

FIG. 24 shows yet another alternate embodiment of the present invention relating to an orthotic device generally indicated as 110 to align and restrict movement of the foot and ankle of a patient relative to the lower leg portion of a patient.

The orthotic device 110 comprises a substantially vertical elongated lateral support member 112 disposed adjacent each side of the patient's lower leg extending between an upper brace member generally indicated as 114 including a concave inner surface 116 configured to engage and partially surround the upper portion of the lower leg below or beneath the knee and a lower foot support generally indicated as 118 including an upper surface 120 configured to engage and support the patient's foot thereon.

As with the other embodiments, the lateral linear dimension 160 of each substantially vertical elongated lateral support member 112 is at least about one and one-half times the longitudinal linear dimension 158 of the outer corresponding substantially vertical elongated lateral support member 112 measured in the horizontal plane allowing the outer substantially vertical elongated lateral support member 112 to flex along the longitudinal axis AA of the lower foot support 118. Preferably the lateral linear dimension 160 of each substantially vertical elongated lateral support member 112 is at least about ⅜ inch.

The upper brace member 114 may be configured to engage the front portion or anterior of the lower leg as shown or the rear portion or posterior of the lower leg with the upper attachment described hereinafter reversed.

The orthotic device 110 is removably secured to the lower patient by an upper attachment member generally indicated as 130.

The upper attachment member 130 comprises a first attachment element 134 such as a strap affixed to the side of upper brace member 114 and a second attachment element 136 such as a buckle or loop affixed to the opposite side of the upper brace member 114 to engage each other to strap the orthotic device 110 to the upper portion of 20 the lower leg of the patient. As best shown in FIG. 12, the strap 134 is fed through the buckle or loop 136 and laid back on itself such that a first fastener such as a plurality of hooks 138 and a second fastener such as a plurality of loops 140 are engaged to each other to secure the upper brace member 114 in place. The upper brace member 114 may comprise a rigid material flexible enough to fit or engage the outside contour of the patient's leg held in place by the upper attachment member 130.

Figure 25:
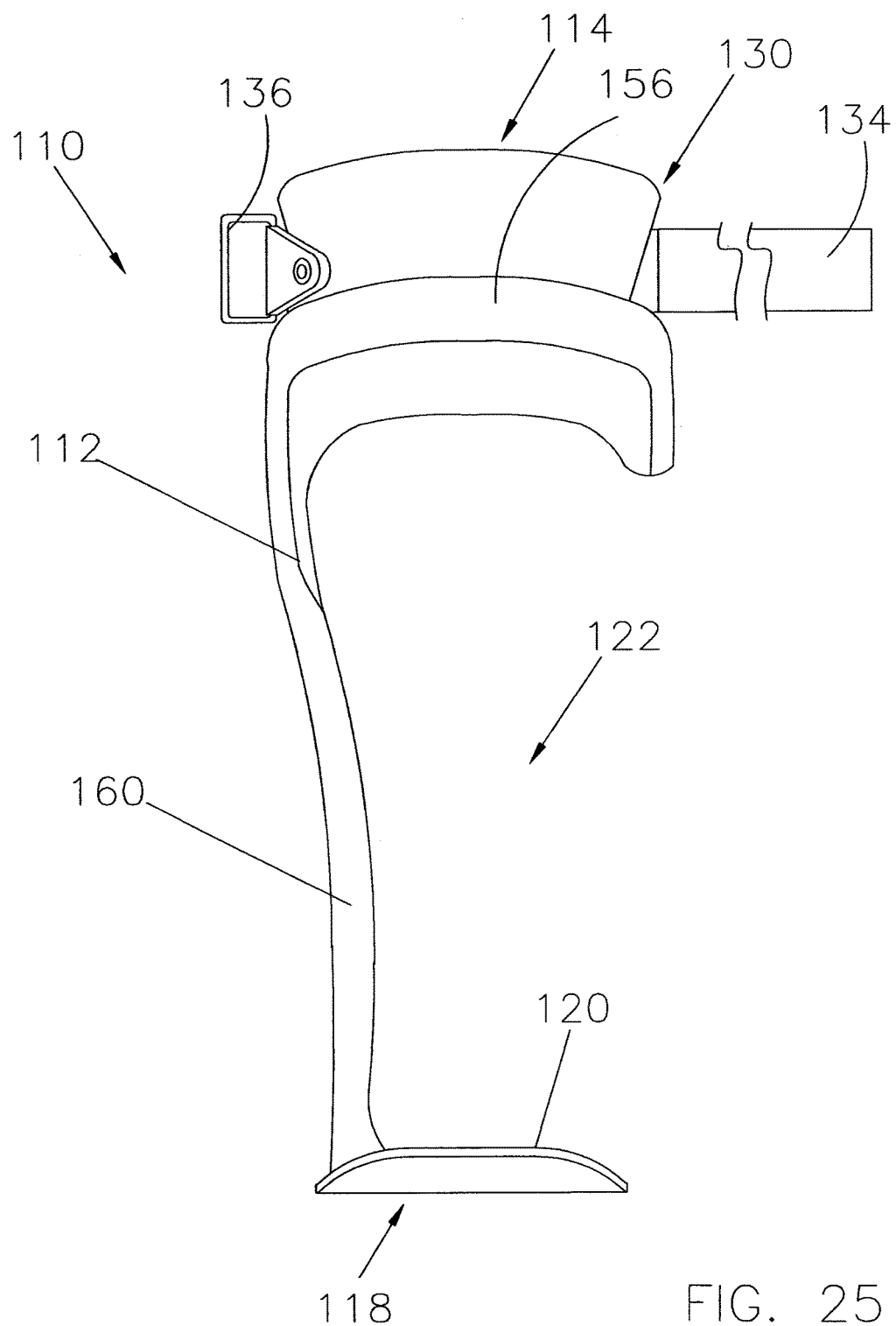
FIG. 25 is a front view of yet another alternate embodiment of the orthotic device of the present invention.

FIG. 25 shows still another alternate embodiment of the present invention relating to an orthotic device generally indicated as 110 to align and restrict movement of the foot and ankle of a patient relative to the lower leg portion of a patient.

The orthotic device 110 comprises a substantially vertical elongated lateral support member 112 disposed adjacent one side of the patient's lower leg extending between an upper brace member generally indicated as 114 including a concave inner surface 116 configured to engage and partially surround the upper portion of the lower leg below or beneath the knee and a lower foot support generally indicated as 118 including an upper surface 120 configured to engage and support the patient's foot thereon.

As with the other embodiments, the lateral linear dimension 160 of the substantially vertical elongated lateral support member 112 is at least about one and one-half times the longitudinal linear dimension of the substantially vertical elongated lateral support member 112 measured in the horizontal plane allowing the substantially vertical elongated lateral support member 112 to flex along the longitudinal axis AA of the lower foot support 118. Preferably the lateral linear dimension 160 of the substantially vertical elongated lateral support member 112 is at least about ⅜ inch.

The upper brace member 114 may be configured to engage the front portion or anterior of the lower leg as shown or the rear portion or posterior of the lower leg with the upper attachment described hereinafter reversed.

The orthotic device 110 is removably secured to the lower patient by an upper attachment member generally indicated as 130 and a lower adjustment member generally indicated as 132.

The upper attachment member 130 comprises a first attachment element 134 such as a strap affixed to the side of upper brace member 114 and a second attachment element 136 such as a buckle or loop affixed to the opposite side of the upper brace member 114 to engage each other to strap the orthotic device 110 to the upper portion of 20 the lower leg of the patient. As best shown in FIG. 12, the strap 134 is fed through the buckle or loop 136 and laid back on itself such that a first fastener such as a plurality of hooks 138 and a second fastener such as a plurality of loops 140 are engaged to each other to secure the upper brace member 114 in place. The upper brace member 114 may comprise a rigid material flexible enough to fit or engage the outside contour of the patient's leg held in place by the upper attachment member 130.

The orthotic device of the present invention is preferably constructed of fabric impregnated with a hardened structural resin.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An orthotic device configured to align and restrict movement of the foot relative to the ankle of a patient relative to the lower leg portion of the patient comprising an elongated lateral support member including an upper and lower portion configured to be disposed on the outside of the patient's lower leg extending between an upper brace member configured to engage and partially surround the upper portion of the lower leg below or beneath the knee, a lower foot support configured to engage and support the foot connected to said elongated lateral support member, a leg engagement member movable from a first position to a second position relative to said elongated lateral support member adapted to be disposed on the inside of the patient's lower leg extending downwardly from said upper brace member terminating in a leg engagement member configured to engage the lower portion on the inside of the patient's leg when said leg engagement member is in said second position, and an upper attachment member to removably secure said orthotic device to the lower leg of the patient and a lower adjustment member configured to substantially encircle the lower leg of the patient to selectively secure said leg engagement member in said second position against the inside of the patient's lower leg forcing the patient's lower leg against said upper and lower portions of said elongated lateral support member configured to restrict the lateral and longitudinal movement of the foot and ankle of the patient relative to the lower of the patient.

2. The orthotic device of claim 1 wherein said elongated lateral support has a lateral linear dimension and a longitudinal linear dimension, said lateral linear dimension of said elongated lateral support is at least about one and one-half times said longitudinal linear dimension of said elongated lateral support member.

3. The orthotic device of claim 2 where said lower foot support includes a heel cup extending upwardly from said top surface thereof.

4. The orthotic device of claim 3 wherein a lateral support member mount extends upwardly from said heel cup to couple said elongated lateral support member to said lower foot support so as the lower portion of elongated lateral support member is adapted to be substantially aligned with the patient's ankle at the point of flexure of said elongated lateral support member.

5. The orthotic device of claim 4 wherein said elongated lateral support member flexes along a longitudinal axis of said lower foot support.

6. The orthotic device of claim 2 wherein said elongated lateral support member is constructed of fabric impregnated with a hardened structural resin.

7. The orthotic device of claim 6 wherein said elongated lateral support member is inclined in a toe out direction relative to the longitudinal axis of said lower foot support so as the patient's lower leg and foot are held in an outwardly direction.

8. The orthotic device of claim 6 wherein said elongated lateral support member is inclined in a toe in direction relative to the longitudinal axis of said lower foot support so as the patient's lower leg and foot are held in an inwardly direction.

9. The orthotic device of claim 2 wherein said elongated lateral support member flexes along the longitudinal axis of said lower foot support.

10. The orthotic device of claim 1 wherein a lateral support member mount extends upwardly from said heel cup to couple said elongated lateral support members to said lower foot support so as the lower portion of said elongated lateral support member is adapted to be substantially aligned with the patient's ankle at the point of flexure of said elongated lateral support member.

11. An orthotic device configured to align and restrict movement of the foot relative to the ankle of a patient relative to the lower leg portion of the patient comprising an elongated lateral support member including an upper and lower portion configured to be disposed on the inside of the patient's lower leg extending between an upper brace member configured to engage and partially surround the upper portion of the lower leg below or beneath the knee, a lower foot support including a top surface and configured to engage and support the foot connected to said elongated lateral support member, a leg engagement member movable between a first position and a second position relative to said elongated lateral support member adapted to be disposed on the outside of the patient's lower leg extending downwardly from said upper brace member terminating in a leg engagement member configured to engage the lower portion on the outside of the patient's leg when said leg engagement member is in said second position, and an upper attachment member adapted to be removably secure said orthotic device to the lower leg of the patient and a lower adjustment member configured to substantially encircle the lower leg of the patient to selectively secure said leg engagement member in said second position against the outside of the patient's lower leg forcing the patient's lower leg against said upper and lower portions of said elongated lateral support member configured to restrict the lateral and longitudinal movement of the foot and ankle of the patient relative to the lower leg of the patient.

12. The orthotic device of claim 11 wherein said elongated lateral support has a lateral linear dimension and a longitudinal linear dimension, said lateral linear dimension of said elongated lateral support is at least about one and one-half times said longitudinal linear dimension of said elongated lateral support member.

13. The orthotic device of claim 12 where said lower foot support comprises a heel cup extending upwardly from said top surface thereof.

14. The orthotic device of claim 13 wherein a lateral support member mount extends upwardly from said heel cup to couple said elongated lateral support member to said lower foot support so as the lower portion of said elongated lateral support member is adapted to be substantially aligned with the patient's ankle at the point of flexure of said elongated lateral support member.

15. The orthotic device of claim 12 wherein said elongated lateral support member is inclined in a toe out direction relative to the longitudinal axis of said lower foot support so as the patient's lower leg and foot are held in an outwardly direction.

16. The orthotic device of claim 12 wherein said elongated lateral support member is inclined in a toe in direction relative to the longitudinal axis of said lower foot support so as the patient's lower leg and foot are held in an inwardly direction.

17. The orthotic device of claim 11 wherein said elongated lateral support member is constructed of fabric impregnated with hardened structural resin.

18. The orthotic device of claim 11 wherein a lateral support member mount extends upwardly from said heel cup to couple said elongated lateral support members to said lower foot support so as the lower portion of said elongated lateral support member is adapted to be substantially aligned with the patient's ankle at the point of flexure of said elongated lateral support member.

19. A leg and foot orthotic device configured to engage both sides of the lower leg and to support the foot of a patient to restrict the lateral and longitudinal movement of the foot relative to the lower leg portion of the patient comprising an elongated lateral support member including an upper and lower portion adapted to be disposed on one side of the patient's lower leg extending between an upper substantially concave rigid brace member configured to engage and partially surround the upper portion of the lower leg, a lower foot support configured to engage and support the foot connected to said elongated lateral support member, a leg engagement member having a lower free end adapted to be disposed the opposite side of the patient's lower leg extending downwardly from said upper substantially concave rigid brace member terminating in a leg engagement member, said leg engagement member adapted to be movable from a first position when in spaced relationship relative to the patient's leg and a second position configured to engage the lower portion of one side of the patient's leg when said leg engagement member is in said second position and an upper attachment member adapted to removably secure said leg and foot orthotic device to the lower leg of the patient and a lower adjustment member configured to substantially encircle the lower leg of the patient to selectively secure said leg engagement member in said second position against the opposite side of the patient's lower leg forcing the patient's lower leg against said upper and lower portions of said lateral support member configured to restrict the lateral and longitudinal movement of the foot and ankle relative to the lower leg of the patient.

\* \* \* \* \*